(12) United States Patent
Euteneuer

(10) Patent No.: US 9,955,968 B2
(45) Date of Patent: May 1, 2018

(54) FASTENERS AND FASTENER DELIVERY DEVICES FOR AFFIXING SHEET-LIKE MATERIALS TO BONE OR TISSUE

(71) Applicant: ROTATION MEDICAL, INC., Plymouth, MN (US)

(72) Inventor: Charles L. Euteneuer, St. Michael, MN (US)

(73) Assignee: ROTATION MEDICAL, INC., Plymouth, MN (US)

(*) Notice: Subject to any disclaimer, the term of this patent is extended or adjusted under 35 U.S.C. 154(b) by 289 days.

(21) Appl. No.: 15/003,381

(22) Filed: Jan. 21, 2016

(65) Prior Publication Data

US 2016/0135806 A1    May 19, 2016

Related U.S. Application Data

(63) Continuation of application No. 13/717,530, filed on Dec. 17, 2012, now Pat. No. 9,271,726.
(Continued)

(51) Int. Cl.
*A61B 17/068* (2006.01)
*A61B 17/064* (2006.01)
(Continued)

(52) U.S. Cl.
CPC ........ *A61B 17/068* (2013.01); *A61B 17/0642* (2013.01); *A61B 17/0682* (2013.01);
(Continued)

(58) Field of Classification Search
CPC .............. A61B 17/068; A61B 17/0642; A61B 17/0644; A61B 17/0682; A61B 17/072;
(Continued)

(56) References Cited

U.S. PATENT DOCUMENTS

| 511,238 A | 12/1893 | Hieatzman et al. |
| 765,793 A | 7/1904 | Ruckel |

(Continued)

FOREIGN PATENT DOCUMENTS

| CA | 2390508 A1 | 5/2011 |
| EP | 0142225 A1 | 5/1985 |

(Continued)

OTHER PUBLICATIONS

Bahler et al., "Trabecular bypass stents decrease intraocular pressure in cultured himan anterior segments," Am. J. Ophthalmology, vol. 138(6), pp. 988-994, Dec. 2004.
(Continued)

*Primary Examiner* — Scott A. Smith
(74) *Attorney, Agent, or Firm* — Seager, Tufte & Wickhem LLP

(57) ABSTRACT

A fastener for attaching a sheet-like implant to tissue or bone may be provided with a first arm having a proximal portion and a distal portion, a second arm having a proximal portion and a distal portion, and a bridge formed at least in part by the proximal portion of the first arm overlapping the proximal portion of the second arm. Each of the first and second arms can include at least a partial loop member having a lumen therethrough slidably receiving the other arm, each arm further including a tissue retention member on a distal portion having a projection extending therefrom for engagement of bone or tissue when inserted therein. The staple can also include a one-way position retention assembly for allowing distal movement of each at least partial loop member relative to the other arm therethrough to tension the fastener and maintain a desired configuration.

13 Claims, 19 Drawing Sheets

Related U.S. Application Data

(60) Provisional application No. 61/577,635, filed on Dec. 19, 2011.

(51) Int. Cl.
*A61B 17/08* (2006.01)
*A61B 17/072* (2006.01)
*A61B 17/00* (2006.01)

(52) U.S. Cl.
CPC ....... *A61B 17/072* (2013.01); *A61B 17/07207* (2013.01); *A61B 17/08* (2013.01); *A61B 2017/00407* (2013.01); *A61B 2017/00668* (2013.01); *A61B 2017/07214* (2013.01)

(58) Field of Classification Search
CPC .............. A61B 17/07207; A61B 17/08; A61B 2017/00407; A61B 2017/00668; A61B 2017/07214
USPC .. 227/19, 175.1, 175.2, 176.1, 179.1, 180.1; 606/139, 143, 151, 153, 219, 213
See application file for complete search history.

(56) References Cited

U.S. PATENT DOCUMENTS

| | | |
|---|---|---|
| 1,728,316 A | 9/1929 | von Wechenfeldt et al. |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,328,077 A | 7/1994 | Lou |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |

(56) References Cited

U.S. PATENT DOCUMENTS

| | | |
|---|---|---|
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Troll |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Troll |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | DiPoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |

(56) References Cited

U.S. PATENT DOCUMENTS

| | | |
|---|---|---|
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 8,579,920 B2 | 11/2013 | Nering et al. |
| 8,668,718 B2 | 3/2014 | Euteneuer et al. |
| 8,702,718 B2 | 4/2014 | Bhatnagar et al. |
| 8,728,099 B2 | 5/2014 | Cohn et al. |
| 8,894,669 B2 | 11/2014 | Nering et al. |
| 9,033,201 B2 | 5/2015 | Euteneuer |
| 9,055,945 B2 | 6/2015 | Miksza et al. |
| 9,107,661 B2 | 8/2015 | Euteneuer |
| 9,125,650 B2 | 9/2015 | Euteneuer |
| 9,198,751 B2 | 12/2015 | Euteneuer et al. |
| 9,247,978 B2 | 2/2016 | Euteneuer et al. |
| 9,271,726 B2 * | 3/2016 | Euteneuer ........... A61B 17/0642 |
| 9,314,314 B2 | 4/2016 | Euteneuer et al. |
| 9,370,356 B2 | 6/2016 | Euteneuer et al. |
| 9,566,063 B2 * | 2/2017 | Euteneuer ........... A61B 17/068 |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0138705 A1 | 7/2004 | Heino et al. |
| 2004/0167519 A1 | 8/2004 | Weiner et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DiMatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer |
| 2012/0248171 A1 | 10/2012 | Bailly et al. |

(56) References Cited

U.S. PATENT DOCUMENTS

| | | |
|---|---|---|
| 2012/0316608 A1 | 12/2012 | Foley |
| 2013/0158661 A1 | 6/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |
| 2013/0245774 A1 | 9/2013 | Euteneuer et al. |

FOREIGN PATENT DOCUMENTS

| | | |
|---|---|---|
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |
| EP | 1559379 A1 | 8/2005 |
| EP | 2030576 A2 | 3/2009 |
| GB | 2154688 A | 9/1985 |
| GB | 2397240 A | 7/2004 |
| JP | 58188442 A | 11/1983 |
| JP | 2005506122 A | 3/2005 |
| JP | 2006515774 A | 6/2006 |
| WO | 8505025 A1 | 11/1985 |
| WO | 0176456 A2 | 10/2001 |
| WO | 0234140 A2 | 5/2002 |
| WO | 03105670 A2 | 12/2003 |
| WO | 2004000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2011095890 A2 | 8/2011 |
| WO | 2011128903 A2 | 10/2011 |

OTHER PUBLICATIONS

Chamay et al., Digital contracture deformity after implantation of a silicone prosthesis: Light and electron microscopic study, The Journal of Hand Surgery, vol. 3(3), pp. 266-270, May 1978.

D'Ermo et al., "Our Results with the operation of ab externo," Ophthalmologica, vol. 168, pp. 347-355, (year of pub. sufficiently earlier than effective US filing date and any foreign priority date) 1971.

France et al., "Biomechanical evaluation of rotator cuff fixation methods," The American Journal of Sports Medicine, vol. 17(2), pp. 176-181, Mar.-Apr. 1989.

Goodship et al., "An assessment of filamentous carbon fibre for the treatment of tendon injury in the horse," Veterinary Record, vol. 17(2) pp. 217-221, Mar. 8, 1980.

Hunter et al., "Flexor-tendon reconstruction in severely damaged hands," The Journal of Bone and Join Surgery (American Volume), voo.54-A(5), pp. 329-358, Jul. 1971.

Johnstone et al., "Microsurgery of Schlemm's Canal and the human aqueous outflow system," Am. J. Ophthalmology, vol. 76(6), pp. 906-917, Dec. 1973.

Kowalsky et al., "Evaluation of suture abrasion against rotator cuff tendon and proximal humerus bone," Arthroscopy, The Journal of Arthoscopic and Related Surgery, vol. 24(3), pp. 329-334, Mar. 2008.

Lee et al., "Aqueous-venous and intraocular pressure. Preliminary report of animal studies," Investigative Ophthalmology, vol. 5(1), pp. 59-64, Feb. 1966.

Mapea et al., "The pressures in the episcleral veins, Schlemm's canal and the trabecular meshwork in monkeys: Effects of changes in intraocular pressure," Exp. Eye Res, vol. 49 pp. 645-663, Oct. 1989.

Nicolle et al., "A silastic ndon prosthesis as an adjunct to flexor tendon grafting . . . ," British Journal of Plastic Surgery, vol. 22(3-4), pp. 224-236 (year of pub. sufficiently earlier than effective US filing date and any foreign priority date) 1969.

Rubin et al., "The use of acellular biologic tissue patches in foot and ankle surgery," Clinics in Podiatric Medicine and Surgery, vol. 22, pp. 533-552, Oct. 2005.

Schultz, "Canaloplasty procedure shows promise for open-angle glaucoma in European study," Ocular Surgery News, pp. 34-35, Mar. 1, 2007.

Spiegel et al., "Schlemm's canal implant: A new method to lower intraocular pressure in patients with POAG," Ophthalmic Surgery and Lasers, vol. 30(6), pp. 492-494, Jun. 1999.

Stetson et al., "Arthroscopic treatment of partial rotator cuff tears," Operative Techniques in Sports Medicine, vol. 12 (2), pp. 135-148, Apr. 2004.

Valdez et al., "Repair of digital flexor tendon lacerations in the horse using carbon fiber implants," JAYMA, vol. 177 (5), pp. 427-435, Sep. 1, 1980.

Wikipedia, the free encyclopedia, Rotator cuff tear, downloaded from <http://en.wikipedia.org/wiki/Rotator_cuff_tear> 14 pages, on Dec. 6, 2012.

Alexander et al., "Ligament and tendon repair with an absorbable polymer-coated carbon fiber stent," Bulletin of the Hospital for Joint Diseases Orthopaedic Institute, vol. 46(2), pp. 155-173, Fall 1986.

* cited by examiner

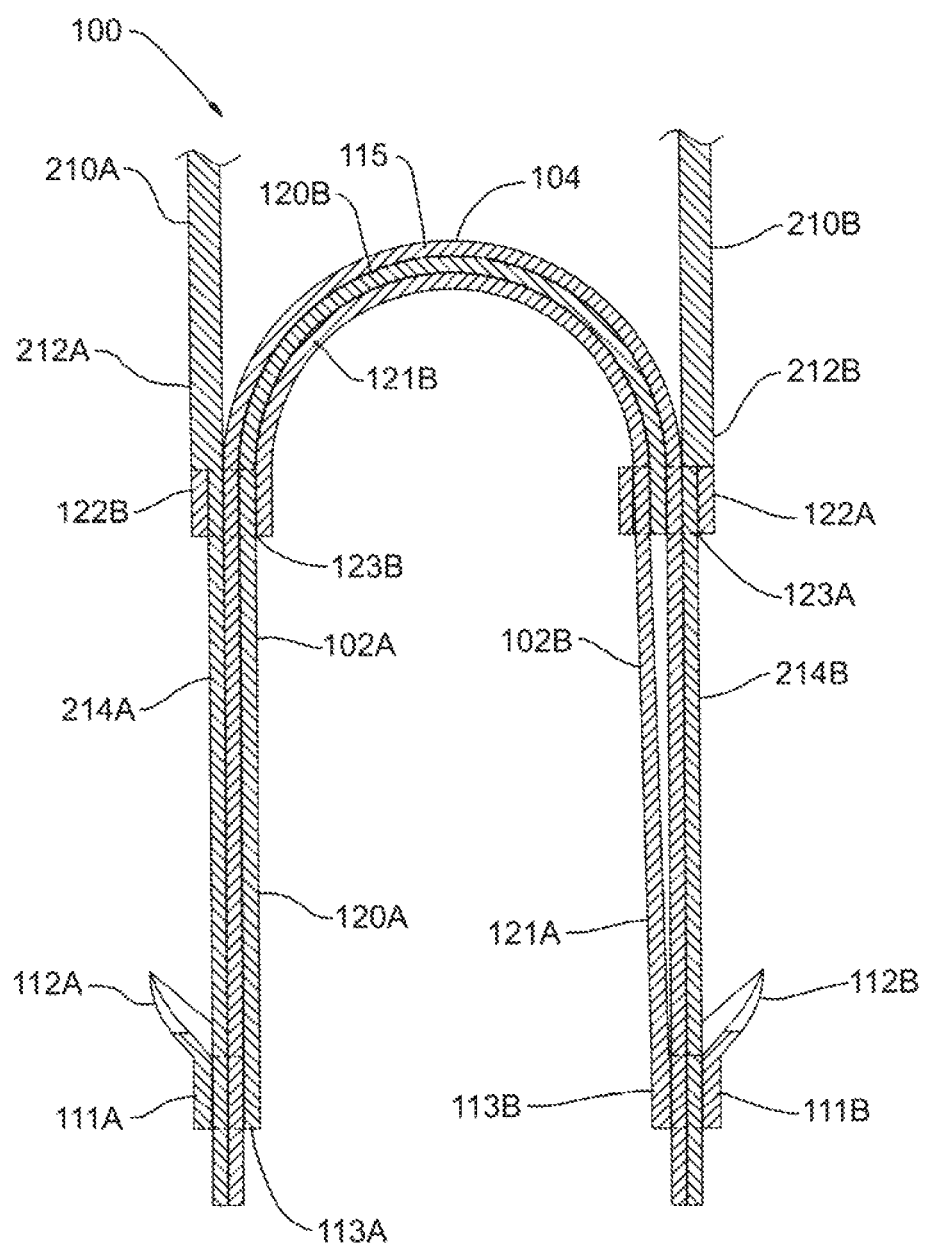

FIG. 3A
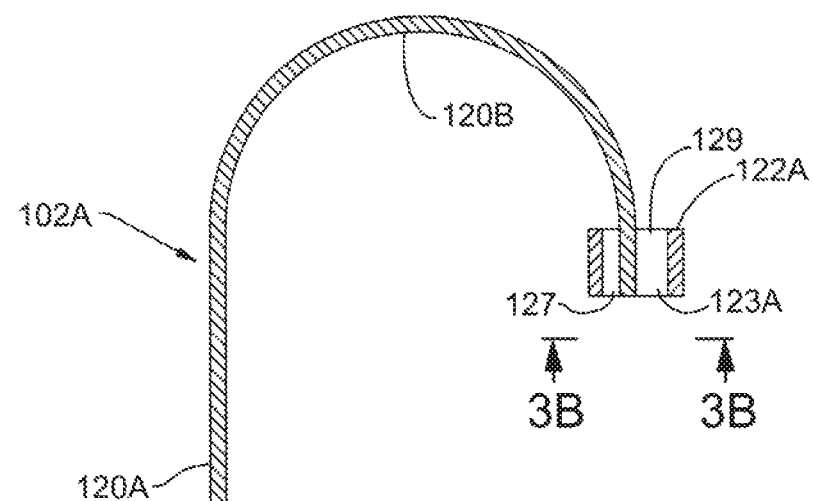
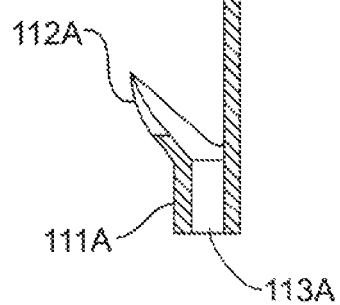
FIG. 3B
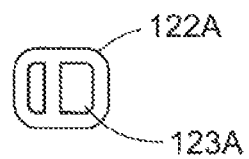

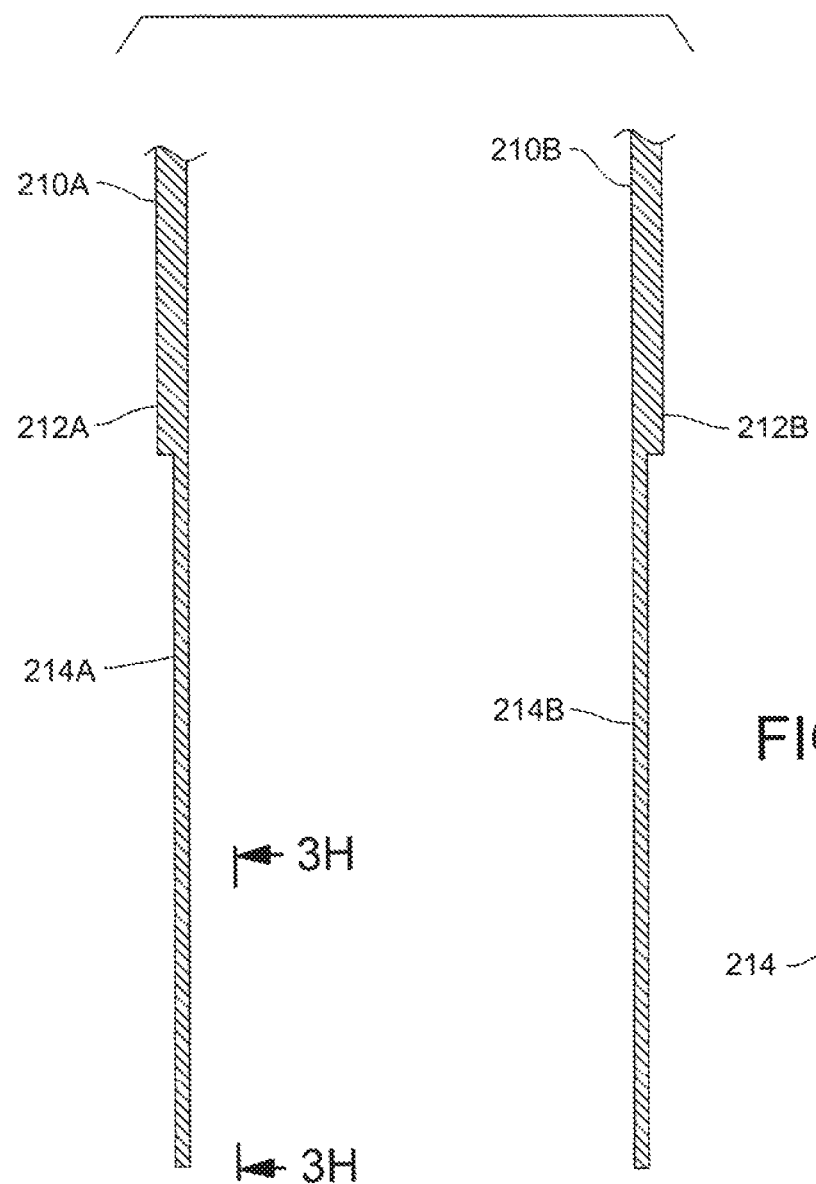

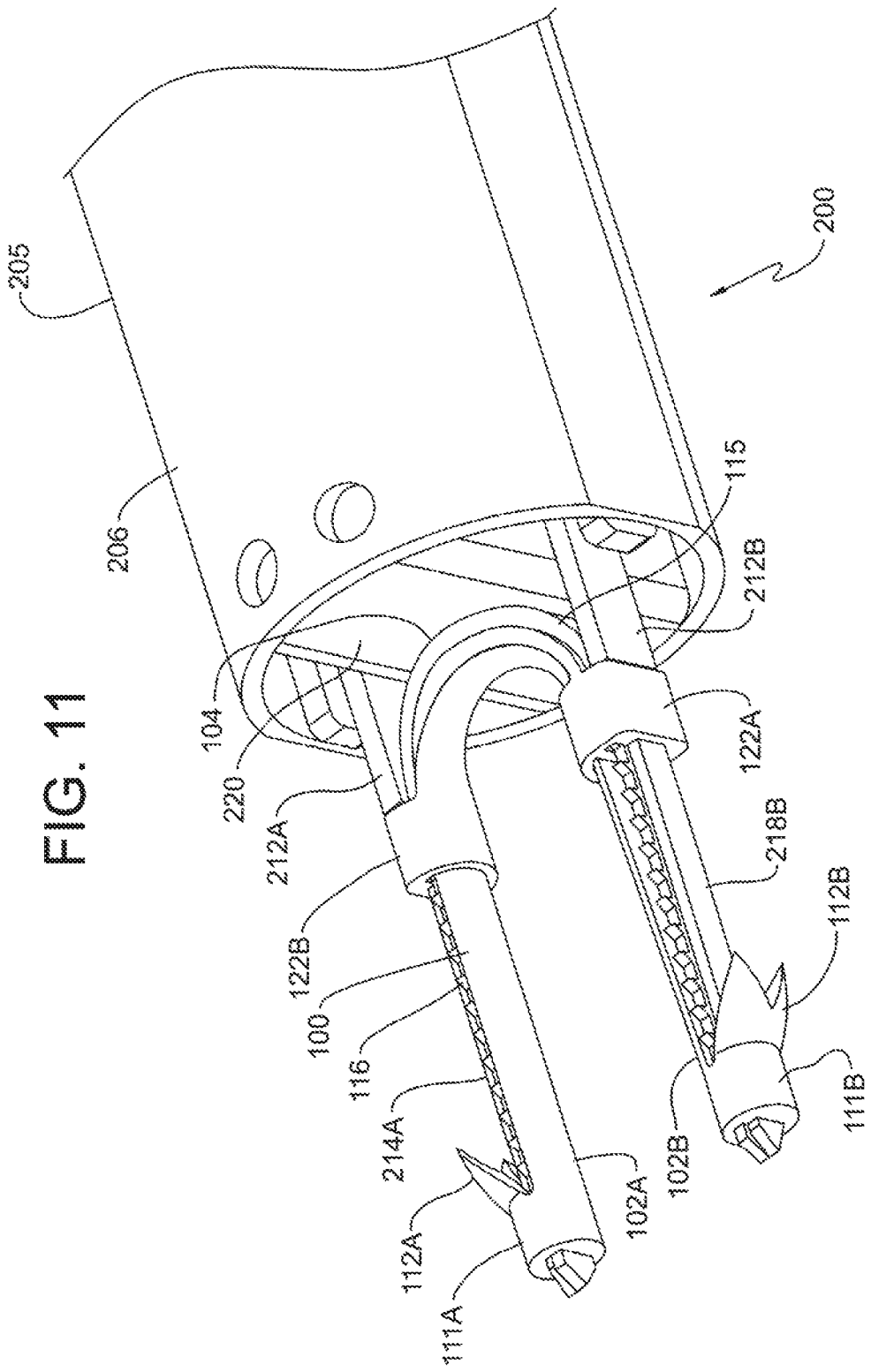

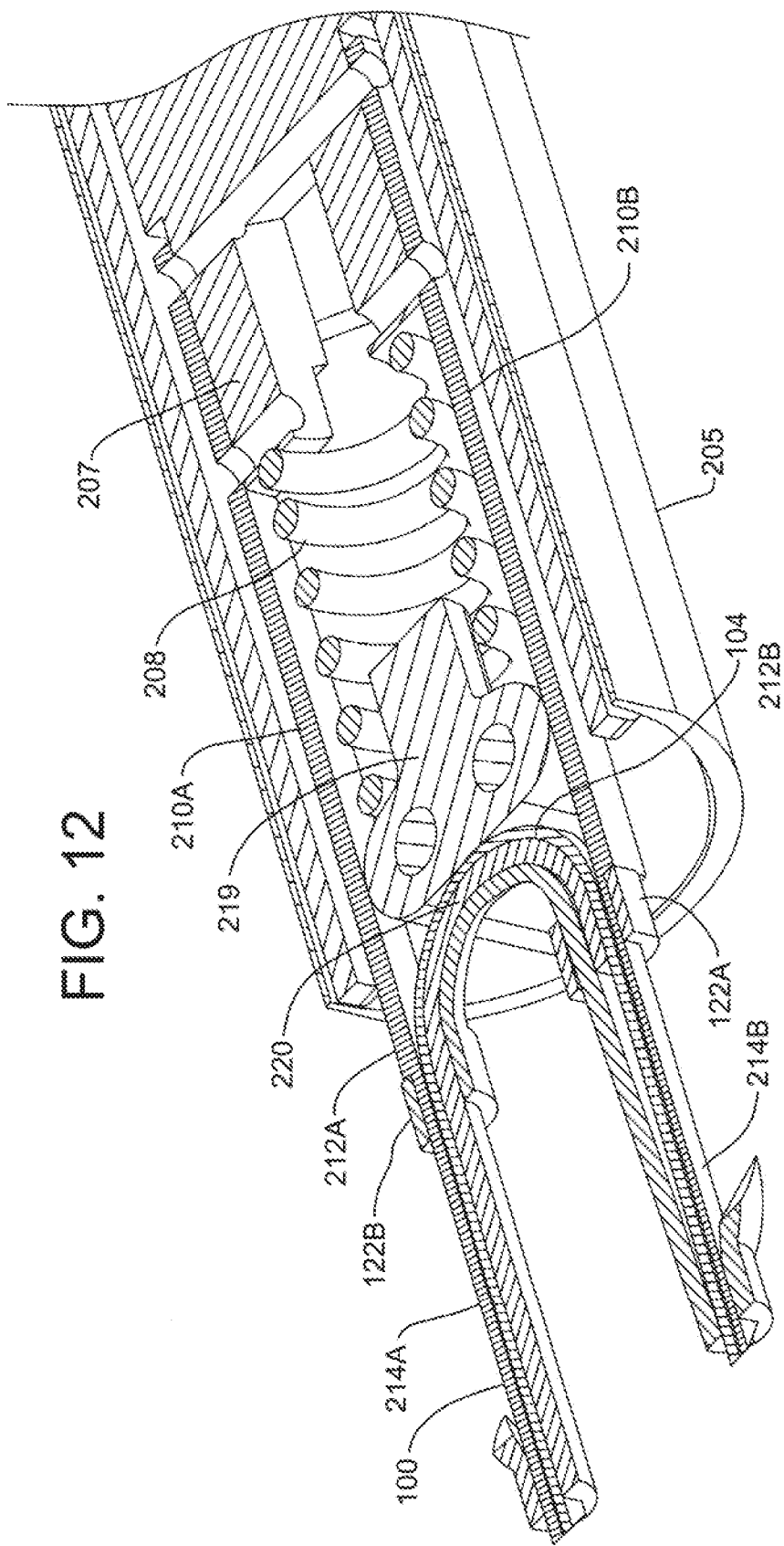

FASTENERS AND FASTENER DELIVERY DEVICES FOR AFFIXING SHEET-LIKE MATERIALS TO BONE OR TISSUE

CROSS REFERENCE TO RELATED APPLICATIONS

This application is a continuation of U.S. application Ser. No. 13/717,530, filed on Dec. 17, 2012, now U.S. Pat. No. 9,271,726, which claims the benefit of U.S. Provisional Patent Application Ser. No. 61/577,635 filed on Dec. 19, 2011, the disclosures of each incorporated herein by reference.

The present disclosure is related to the following commonly assigned co-pending applications, the disclosures of which are incorporated herein by reference: U.S. Provisional Application No. 61/577,621 filed on Dec. 19, 2011; U.S. Provisional Application No. 61/577,626 filed on Dec. 19, 2011; and U.S. Provisional Application No. 61/577,632 filed on Dec. 19, 2011.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to orthopedic medicine and surgery. More particularly, the present invention relates to methods and apparatus for forming pilot holes in bone for inserting fasteners and fixation of sheet-like materials, such as for treating tendons or like tissue of articulating joints, such as tendons in the rotator cuff of the shoulder.

BACKGROUND

The glenohumeral joint of the shoulder is found where the head of the humerus mates with a shallow depression in the scapula. This shallow depression is known as the glenoid fossa. Six muscles extend between the humerus and scapula and actuate the glenohumeral joint. These six muscles include the deltoid, the teres major, and the four rotator cuff muscles. The rotator cuff muscles are a complex of muscles. The muscles of the rotator cuff include the supraspinatus, the infraspinatus, the subscapularis, and the teres minor. The centering and stabilizing roles played by the rotator cuff muscles are critical to the proper function of the shoulder. The rotator cuff muscles provide a wide variety of moments to rotate the humerus and to oppose unwanted components of the deltoid and pectoral muscle forces.

The muscles of the rotator cuff arise from the scapula. The distal tendons of the rotator cuff muscles splay out and interdigitate to form a common continuous insertion on the humerus. The supraspinatus muscle arises from the supraspinatus fossa of the posterior scapula, passes beneath the acromion and the acromioclavicular joint, and attaches to the superior aspect of the greater tuberosity. The mechanics of the rotator cuff muscles are complex. The rotator cuff muscles rotate the humerus with respect to the scapula, compress the humeral head into the glenoid fossa providing a critical stabilizing mechanism to the shoulder (known as concavity compression), and provide muscular balance. The supraspinatus and deltoid muscles are equally responsible for producing torque about the shoulder joint in the functional planes of motion.

The rotator cuff muscles are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear at the insertion site of the tendon with the humerus, may result in the detachment of the tendon from the bone. This detachment may be partial or full, depending upon the severity of the injury or damage. Additionally, the strain or tear can occur within the tendon itself. Injuries to the supraspinatus tendon and current modalities for treatment are defined by the type and degree of tear. The first type of tear is a full thickness tear, which as the term indicates is a tear that extends through the thickness of the supraspinatus tendon regardless of whether it is completely torn laterally. The second type of tear is a partial thickness tear which is further classified based on how much of the thickness is torn, whether it is greater or less than about 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In contrast to the treatment of a full thickness tear or a partial thickness tear of greater than 50%, the current standard treatment for a partial thickness tear less than 50% usually involves physical cessation from use of the tendon, i.e., rest. Specific exercises can also be prescribed to strengthen and loosen the shoulder area. In many instances, the shoulder does not heal and the partial thickness tear can be the source of chronic pain and stiffness. Further, the pain and stiffness may cause restricted use of the limb which tends to result in further degeneration or atrophy in the shoulder. Surgical intervention may be required for a partial thickness tear of less than 50%, however, current treatment interventions do not include repair of the tendon, and rather the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure in which tendon material is ablated. Again, the tendon partial thickness tear is not repaired. Several authors have reported satisfactory early post operative results from these procedures, but over time recurrent symptoms have been noted. In the event of recurrent symptoms, many times a patient will "live with the pain". This may result in less use of the arm and shoulder which causes further degeneration of the tendon and may lead to more extensive damage. A tendon repair would then need to be done in a later procedure if the prescribed treatment for the partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate treatments do not currently exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. Further, it would be beneficial to be able to treat partial thickness tears greater than 50% without cutting the untorn portion of the tendon to complete the tear before suturing back together. There is a large need for surgical techniques and systems to treat partial thickness tears and prevent future tendon damage by strengthening or repairing the native tendon having the partial thickness tear.

SUMMARY OF THE DISCLOSURE

The present disclosure is generally directed to a fastener or staple that can be used to attach an implant to bone or other tissue. The staple or fastener can be included in a kit or system that also can include a staple delivery device and a pilot hole forming trocar assembly. The trocar assembly is used to create pilot holes and retain instrument position within those pilot holes for staple insertion. The staple delivery device can carry the staple into the pilot holes and release the staple in engagement with bone to retain the implant in position.

The staple for insertion and retention in bone can include a bridge portion having arms extending from proximate each end thereof. The staple can include a first arm having a proximal portion and a distal portion, a second arm having a proximal portion and a distal portion, and a bridge formed at least in part by the proximal portion of the first arm overlapping the proximal portion of the second arm. Each of the first and second arms can include at least a partial loop member having a lumen therethrough slidably receiving the other arm, each arm further including a tissue retention member on a distal portion having a projection extending therefrom for engagement of bone when inserted therein. The loop can be a full loop having a lumen therethrough, with the diameter of the loop extending laterally from the arm on which it is formed or attached.

Each tissue retention member can have a lateral extent larger than the arm proximal thereto to provide a change in lateral stiffness to allow flexing of each arm adjacent the tissue retention member in response to a pullout force. Further, each projection can extend proximally and laterally away from its respective arm. Each of the tissue retention members can have a lumen extending longitudinally therethrough.

A staple of the present disclosure can also include a one-way position retention assembly for allowing distal movement of each at least partial loop member relative to the other arm therethrough to tension the fastener and maintain a desired configuration. In some embodiments, the one-way position retention assembly can include a generally U-shaped strap having a toothed surface along at least a portion of the length thereof that passes through the lumen of the tissue retention members and engages a surface therein that allows distal movement of the U-shaped strap while preventing proximal movement. Alternatively, the one-way position retention assembly can include a projection within the at least partial loop of each arm wherein the projection engages a toothed surface on the arm extending therethrough to allow distal movement of the loop along the arm while preventing or restricting proximal movement.

The present disclosure is also directed to a fastener delivery tool. The fastener delivery tool can include a barrel assembly having an outer sheath with a staple delivery assembly disposed therein, the staple delivery assembly including a shaft having a distal surface for the engagement of a bridge portion of a staple when mounted on the delivery tool. The staple delivery assembly can further include a pair of staple setting rods extending along the length of the shaft each having stake portions extending distally beyond the distal surface.

Each stake portion can include a distal portion sized for sliding engagement of a tissue retention member and a proximal portion having a surface abutting a loop member on a staple arm for applying distally directed force to the loop to achieve a desired configuration of the staple retained in tissue when the stakes are moved distally relative to the surface. The barrel can be mounted to a handle assembly fixed to the outer sheath of the barrel in operative relationship with the staple delivery assembly.

The staple delivery assembly can be longitudinally extendable from a first position enclosed within the sheath to a second position wherein at least a portion of the staple delivery assembly extends distally from the sheath. The staple delivery assembly can include a proximal shaft portion having a proximal portion of the staple setting rods fixed thereto and a distal portion with a spring therebetween to allow relative longitudinal movement between the distal surface and the staple setting rods in response to increased force on the proximal end of the staple delivery assembly. Further, at least a portion of the staple setting rods can have a cross sectional shape that slidingly engages a channel of like cross sectional shape on the staple delivery assembly to restrict relative motion of the surface and staple setting rods in the longitudinal direction.

BRIEF DESCRIPTION OF THE DRAWINGS

FIG. 2 is a an alternative cross sectional plan view of the staple of FIG. 1 depicting the components of the staple in one embodiment;

FIGS. 3A-3H are plan views of the various components that can be assembled to form the staple of FIG. 1;

FIG. 11 is a perspective view depicting the distal portion of a staple delivery tool or device of the present disclosure having a staple mounted thereon and a staple delivery assembly extending beyond the barrel;

FIG. 12 is partial cross sectional perspective view of the distal portion depicted in FIG. 11 showing the surface engaging the bridge of the staple and staple setting rods engaging the proximal surface of the staple loops;

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

Figure 1:
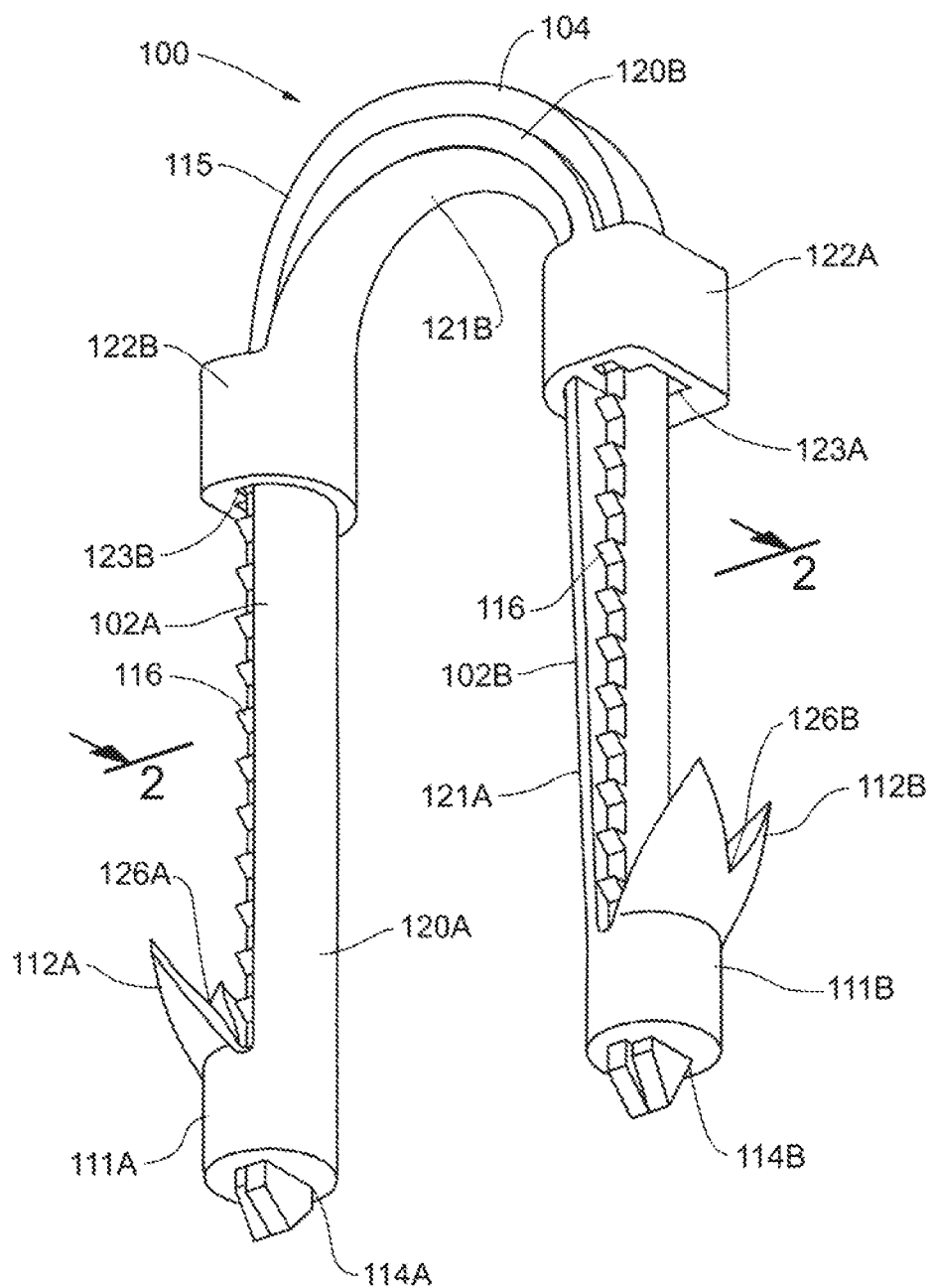
FIG. 1 is a perspective view illustrating an exemplary tissue fastener or staple in accordance with the present disclosure.

FIG. 1 is a perspective view illustrating an exemplary staple 100 in accordance with the present detailed description. With reference to FIG. 1, it will be appreciated that staple 100 may assume various orientations without deviating from the spirit and scope of this detailed description. Although the various parts of this exemplary embodiment are depicted in relative proportion to other parts of the staple 100, other configurations in size and orientation of the various parts are possible.

Staple 100 comprises a first arm 102A, a second arm 102B, and a bridge 104. As illustrated, the bridge 104 is formed, at least in part by a portion of the first arm 102A and second arm 102B. Each arm includes a distal portion 120A, 121A and proximal portion 120B, 121B with the proximal portions of each arm overlapping the other to form a portion of the bridge 104. As configured, the arms can slide relative to each other along the proximal portions of the arms.

With continued reference to FIG. 1, each of the arms 102A, 102B include at least a partial loop member 122A, 122B on the respective arms. The loop may be partial or complete (as depicted in FIG. 1). In some embodiments the loop is located at the end of the proximal portion 120B, 121B of each arm 102A, 102B. Each loop includes a lumen 123A, 123B extending therethrough, respectively. A part of the proximal portion 120B, 121B of the other arm is disposed through the lumen of the loop and can slide therein.

The distal portion 120A, 121A of each arm 102A, 102B includes a tissue retention member 111A, 111B. Each tissue retention member has at least one projection 112A, 112B extending therefrom. The tissue retention members can be attached to or integrally molded with a distal portion of its respective arm 102A, 102B. As illustrated, each of the tissue retention members 111A, 111B have a lateral extent larger than the arm proximal thereto to provide a change in lateral stiffness to allow flexing of each arm adjacent the tissue retention member in response to a pullout force. Further, each projection extends proximally and laterally away from its respective arm to engage bone when placed therein. In some embodiments of the present disclosure each tissue retention member can include a longitudinally extending lumen 114A, 114B extending therethrough.

As also depicted in FIG. 1, a fastener of the present disclosure can include a one-way position retention assembly 115 for allowing distal movement of each at least partial loop member 122A, 122B relative to the other arm therethrough to tension the fastener and maintain a desired configuration. The one-way position retention assembly 115 can include a generally U-shaped strap having a toothed surface 116 along at least a portion of the length thereof that passes through the lumen of the tissue retention members and engages a surface therein that allows distal movement of the U-shaped strap while preventing proximal movement. For example, the inside surface of the tissue retention members can include a projection that interacts with the toothed surface to allow the U-shaped strap to move distally therethrough but will prevent or restrain the U-shaped strap from moving proximally.

Alternatively, the one-way position retention assembly can include a projection within the at least partial loop of each arm wherein the projection engages a toothed or textured surface on the arm extending therethrough to allow distal movement of the loop along the arm while preventing proximal movement. In this embodiment the U-shaped strap is not necessary.

In some embodiments, the components of the staple are each molded from a polymer material such as a polyether ether ketone (PEEK) or a biodegradable polymer such as polylactic acid (PLA) or polyglycolic acid (PGA) and mixtures thereof. Alternatively, staple components can be cut from tubular polymeric stock.

In some useful embodiments, each projection 112A, 112B of staple 100 may be clefted to form a plurality of points for greater retention in tissue. In the exemplary embodiment of FIG. 1, first projection 112A defines a first notch 126A that divides first projection 112A into a first sub-projection and a second sub-projection. Second projection 112B defines a second notch 126B. In the exemplary embodiment of FIG. 1, second notch 126B divides second projection 112B into a first sub-projection and a second sub-projection.

Figure 3C:
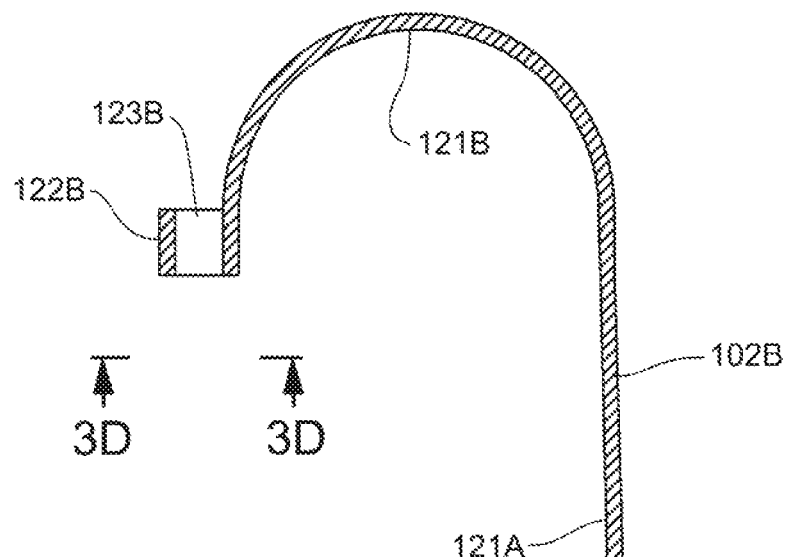
Figure 3D:
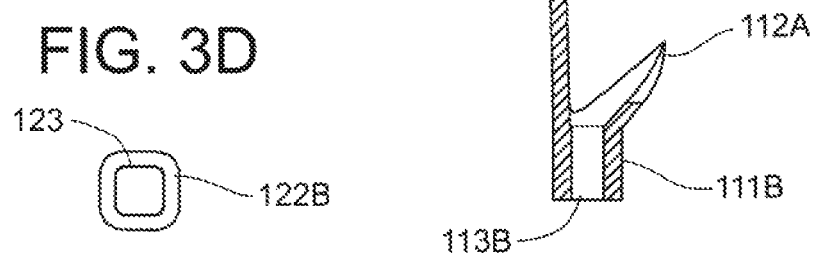

Referring now to FIG. 2, the staple or fastener 100 of FIG. 1 is depicted in cross sectional plan view to better illustrate the staple components and how they are assembled to function in embodiments of the present disclosure. In the assembled cross sectional view of FIG. 2, the staple 100 includes the following components: a first arm 102A; a second arm 102B and one-way position retention assembly 115. Each of these three components is shown individually in partial cross sectional plan view prior to assembly with the other components in FIGS. 3A-3B; FIGS. 3C-3D; and, FIGS. 3E-3F, respectively. Further, the stakes of a distal portion of a staple setting rod are depicted relative to the staple as it is mounted on the stakes for insertion into bone. This component is shown individually in FIGS. 3G-3H and also described in more detail with respect to FIGS. 11-12.

The first component of one embodiment of a staple of the present disclosure is a first arm 102A as noted in the assembled staple of FIG. 2 and shown individually in FIGS. 3A-3B. The first arm 102A can include a length of polymeric material that is flexible and can be formed into a desired curved shape. Alternatively, the first arm 102A can be molded to a desired curved shape as depicted in FIG. 3A. In general, the first arm 102A can include a distal portion 120A that can be relatively straight with a tissue retention member 111A disposed proximate the distal end of the first arm 102A.

The tissue retention member 111A can include a projection or barb 112A extending at least in part laterally from the tissue retention member in order to contact bone and provide resistance to pullout when the staple is under tension. Further, the tissue retention member 111A can include a longitudinally extending lumen 113A extending therethrough. The longitudinally extending lumen 113A can be sized for receiving a distal portion 214A of a staple setting rod 210A. The staple setting rod 210A distal portion 214A can provide longitudinal support for the staple 100 during insertion into pilot holes that have been formed in bone. The lumen 113A can also receive a distal portion of a U-shaped member 115 that, as described below, retains the staple 100 in a selected configuration after deployment. As illustrated, the staple retention member 111A can include a lateral extent or cross section greater than the cross section of the arm adjacent thereto. This can result in a change in flexibility that allows the projections or barbs to better grasp the bone and retain position in the pilot hole.

The proximal portion 120B of the first arm 102A can be curved to form a portion of the bridge 104 of the staple 100. In some embodiments, a loop 122A (which may be partial or whole) is disposed near the proximal end of the proximal portion 120B of the first arm 102A. The loop 122A includes at least one lumen 123A extending therethrough. As depicted, the loop includes a first lumen 127 that is spaced laterally toward the center of the staple inside the place of termination of the arm. This provides a lumen for receiving the second arm therethrough as discussed below. The loop 122A also includes a second lumen 129 which extends laterally away from the center of the staple outside the place of termination of the arm. This lumen allows both the U-shaped member 115 and the distal portion 214B of the stake 210B to extend therethrough.

The second component of one embodiment of a staple of the present disclosure is a second arm 102B as noted in the assembled staple of FIG. 2 and shown individually in FIGS. 3C-3D. The second arm 102B can include a length of polymeric material that is flexible and can be formed into a desired curved shape. Alternatively, the second arm 102B can be molded to a desired curved shape as depicted in FIG. 3C. In general, the second arm 102B can include a distal portion 121A that can be relatively straight with a tissue retention member 111B disposed proximate the distal end of the second arm 102B.

The tissue retention member 111B can include a projection or barb 112B extending at least in part laterally from the tissue retention member in order to contact bone and provide resistance to pullout when the staple is under tension. Further, the tissue retention member 111B can include a longitudinally extending lumen 113B extending therethrough. The longitudinally extending lumen 113B can be sized for receiving a distal portion 214B of a staple setting rod 210B. The staple setting rod 210B distal portion 214B can provide longitudinal support for the staple 100 during insertion into pilot holes that have been formed in bone. The lumen 113B can also receive a distal portion of a U-shaped member 115 that, as described below, retains the staple 100 in a selected configuration after deployment. As illustrated, the staple retention member 111B can include a lateral extent or cross section greater than the cross section of the arm adjacent thereto. This can result in a change in flexibility that allows the projections or barbs to better grasp the bone and retain position in the pilot hole.

The proximal portion 121B of the first arm 102B can be curved to form a portion of the bridge 104 of the staple 100. In some embodiments, a loop 122B (which may be partial or whole) is disposed near the proximal end of the proximal portion 121B of the second arm 102b. The loop 122B includes at least one lumen 123B extending therethrough. As depicted, the lumen 123B extends laterally away from the center of the staple outside the place of termination of the arm. This lumen allows the U-shaped member 115, a portion of the other arm 102A and the distal portion 214A of the stake 210A to extend therethrough.

Figure 3E:
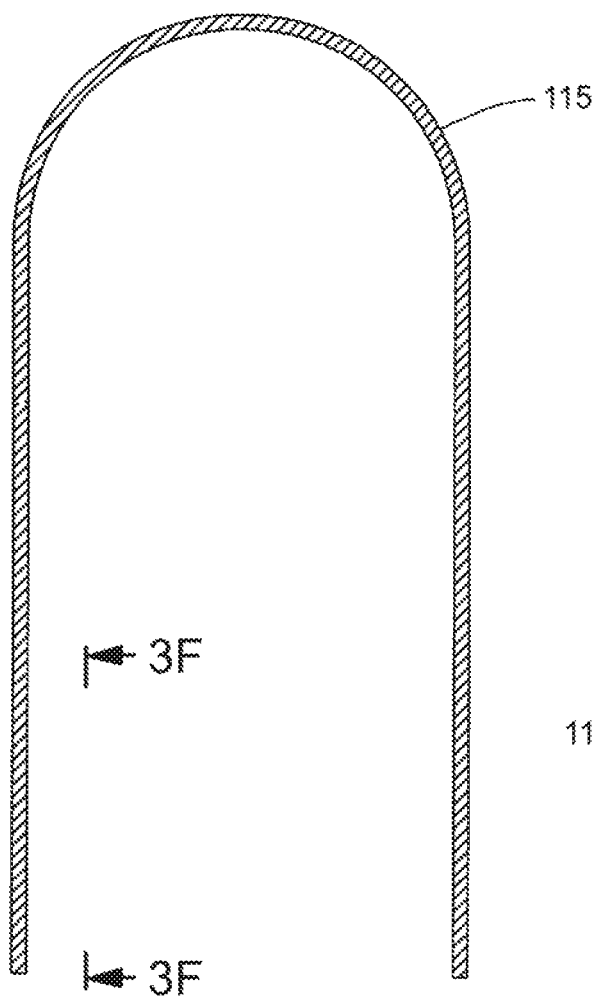
Figure 3F:
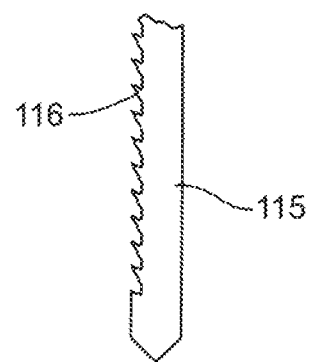

The third component of the staple 100 can be a generally U-shaped strap 115 as depicted assembled in FIG. 2 and individually as a component in FIGS. 3E-3F. As described above, the two arms of the staple include loops through which the other arm passes. This allows the effective length of the arms to be changed as more or less of the two arms overlap each other. The adjustable design allows the overall size of the staple to be adjusted so that the bridge is in tension after insertion. The design also allows the length of an individual leg to be shortened if the inserted leg is not engaged with sufficient holding strength in a portion of a bone that is too porous. The arm may be shortened to the point where the tissue retention member engages the inside surface of the cortical bone layer.

The U-shaped strap 115 functions to retain the staple in a selected configuration. As depicted, the U-shaped strap extends over the bridge 104 and includes legs that extend along the straight portions of the arms through the loops and the lumen of each tissue retention member. The U-shaped strap 115 can include a serrated or toothed surface 116 that interacts with a projection within the lumen of each tissue retention member allowing the U-shaped strap to move distally relative to the arms or the arm to move proximally relative to the U-shaped strap. Likewise, the toothed surface prevents or restricts movement of the U-shaped strap proximally or the arms distally.

In one alternative embodiment, the generally U-shaped strap can be eliminated by incorporating the functional aspects of this strap into the individual loops and arms. In particular, each of the loops can include a projection or other element that interacts with notches or teeth formed on the surface of the other arm passing therethrough. The combination would allow the overall length of the staple or individual arm length to be shortened while restricting or preventing each arm from lengthening.

A cross section of a portion of the stakes 210A, 210B are depicted in FIGS. 3G-3H. The stakes include a distal portion 214A, 214B of smaller cross section than a proximal portion 212A, 212B. As illustrated in FIG. 2, the distal portions 214 extend through the loops of the arms and the lumens of the tissue retention members. The cross section of the proximal portion 212 is larger than the lumen of the loop so that a proximal surface of the loop abuts a distal surface of the proximal portion 212 of the stake 210. Force applied to the interface between these surfaces causes either the bridge to move distally or the tissue retention member opposite the loop to move proximally. As previously stated, this motion allows the staple to be configured after being placed in the pilot holes so that the bridge is in tension while the projections of the tissue retention members are engaged sufficiently in competent bone material.

Figure 4:
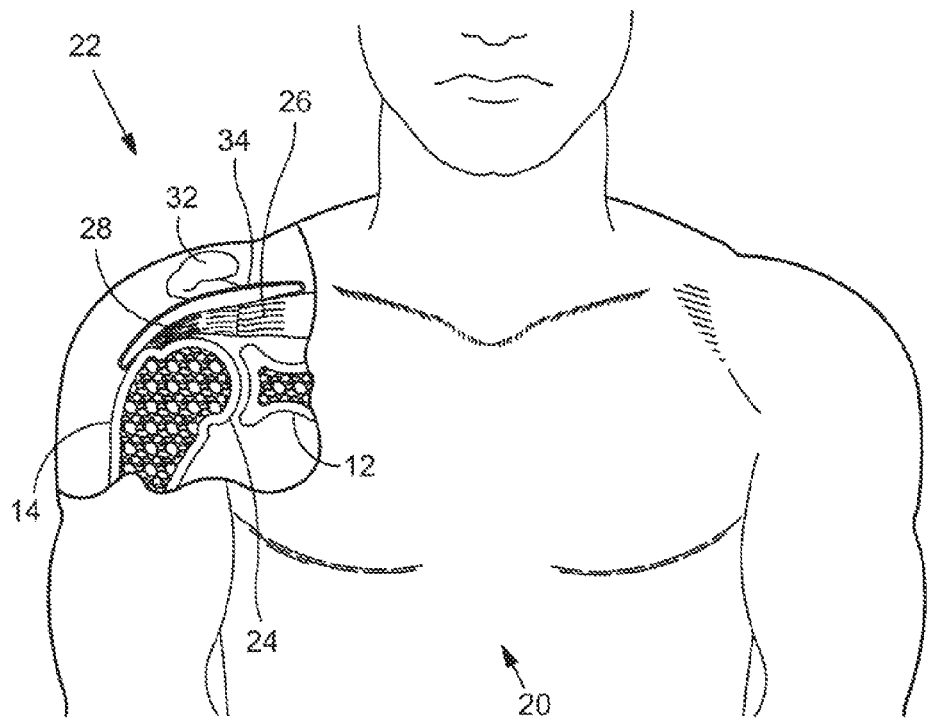
FIG. 4 is a stylized anterior view of a shoulder including a humerus and a scapula.

Next referring to FIG. 4, an exemplary use or application of the staples of the present disclosure is described. FIG. 4 is a stylized anterior view of a patient 20. For purposes of illustration, a shoulder 22 of patient 20 is shown in cross-section in FIG. 4. Shoulder 22 includes a humerus 14 and a scapula 12. In FIG. 4, a head 24 of humerus 14 can be seen mating with a glenoid fossa of scapula 12 at a glenohumeral joint. With reference to FIG. 4, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 4.

With reference to FIG. 4, a distal tendon 28 of the supraspinatus 26 meets humerus 14 at an insertion point. Scapula 12 of shoulder 22 includes an acromium 32. In FIG. 4, a subacromial bursa 34 is shown extending between acromium 32 of scapula 12 and head 24 of humerus 14. Subacromial bursa 34 is shown overlaying supraspinatus 26 as well as supraspinatus tendon 28 and a portion of humerus 14. Subacromial bursa 34 is one of the hundreds of bursae found the human body. Each bursa comprises a fluid filled sac. The presence of these bursae in the body reduces friction between bodily tissues.

The exemplary staples or fasteners described herein may be used to affix tendon repair implants to various target tissues. The shoulder depicted in FIG. 4 is one example where a tendon repair implant may be affixed to one or more bones associated with an articulating joint, such as the glenohumeral joint. Additionally, the tendon repair implant may be affixed to one or more tendons to be treated. The tendons to be treated may be torn, partially torn, have internal micro-tears, be untorn, and/or be thinned due to age, injury or overuse. Applicants believe that the methods and apparatus of the present application and related devices may provide very beneficial therapeutic effect on a patient experiencing joint pain believed to be caused by partial thickness tears and/or internal microtears. By applying a tendon-repair implant early before a full tear or other injury develops, the implant may cause the tendon to thicken and/or at least partially repair itself, thereby avoiding more extensive joint damage, pain, and the need for more extensive joint repair surgery.

Figure 5:
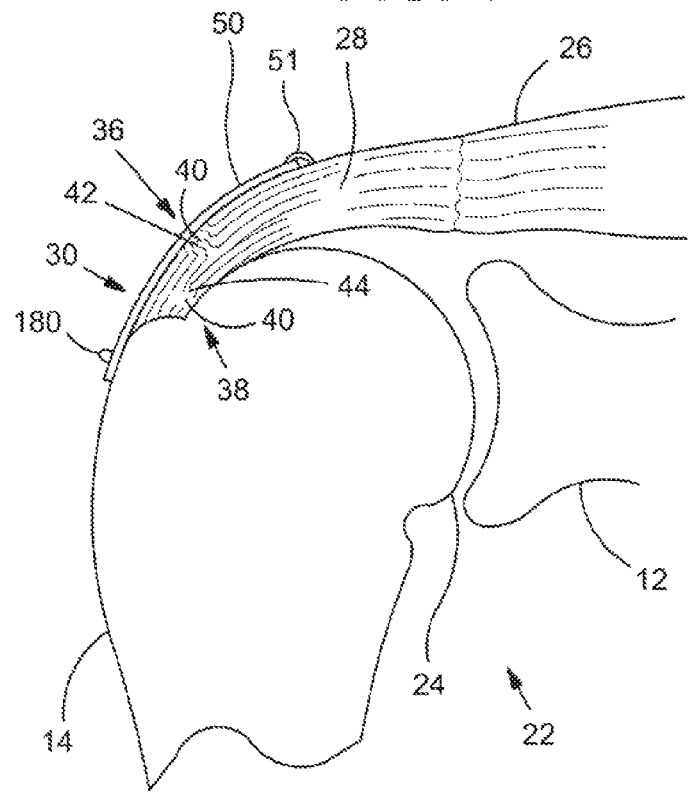
FIG. 5 is a stylized view of a shoulder depicting the head of the humerus shown mating with the glenoid fossa of the scapula at a glenohumeral joint and a sheet-like material is affixed to the tendon.

FIG. 5 is a stylized anterior view of a shoulder 22 including a humerus 14 and a scapula 12. In FIG. 5, a head 24 of humerus 14 is shown mating with a glenoid fossa of scapula 12 at a glenohumeral joint. A supraspinatus 26 is also shown in FIG. 5. This muscle, along with others, controls the movement of humerus 14 relative to scapula 12. A distal tendon 28 of supraspinatus 26 meets humerus 14 at an insertion point 30.

As depicted in FIG. 5, distal tendon 28 includes a first damaged portion 36. A number of loose tendon fibers 40 in first damaged portion 36 are visible in FIG. 5. First damaged portion 36 includes a first tear 42 extending partially through distal tendon 28. First tear 42 may therefore be referred to as a partial thickness tear. With reference to FIG. 5, first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 5, distal tendon 28 includes a second damaged portion 38 located near insertion point 30. As illustrated, second damaged portion 38 of distal tendon 28 has become frayed and a number of loose tendon fibers 40 are visible. Second damaged portion 38 of distal tendon 28 includes second tear 44. Second tear 44 begins on the side of distal tendon 28 facing the center of the humeral head 24. Accordingly, second damaged portion 38 may be referred to as an articular side tear.

FIG. 5 illustrates a sheet-like implant 50 has been placed over the bursal side of distal tendon 28. The sheet-like implant 50 is affixed to distal tendon 28 by a plurality of tendon staples 51. Sheet-like implant 50 is affixed to humerus 14 by a plurality of bone staples 100 in accordance with designs of staples disclosed herein. Sheet-like implant 50 extends over insertion point 30, first tear 42 and second tear 44. Some useful methods in accordance with this detailed description may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon.

Figure 6:
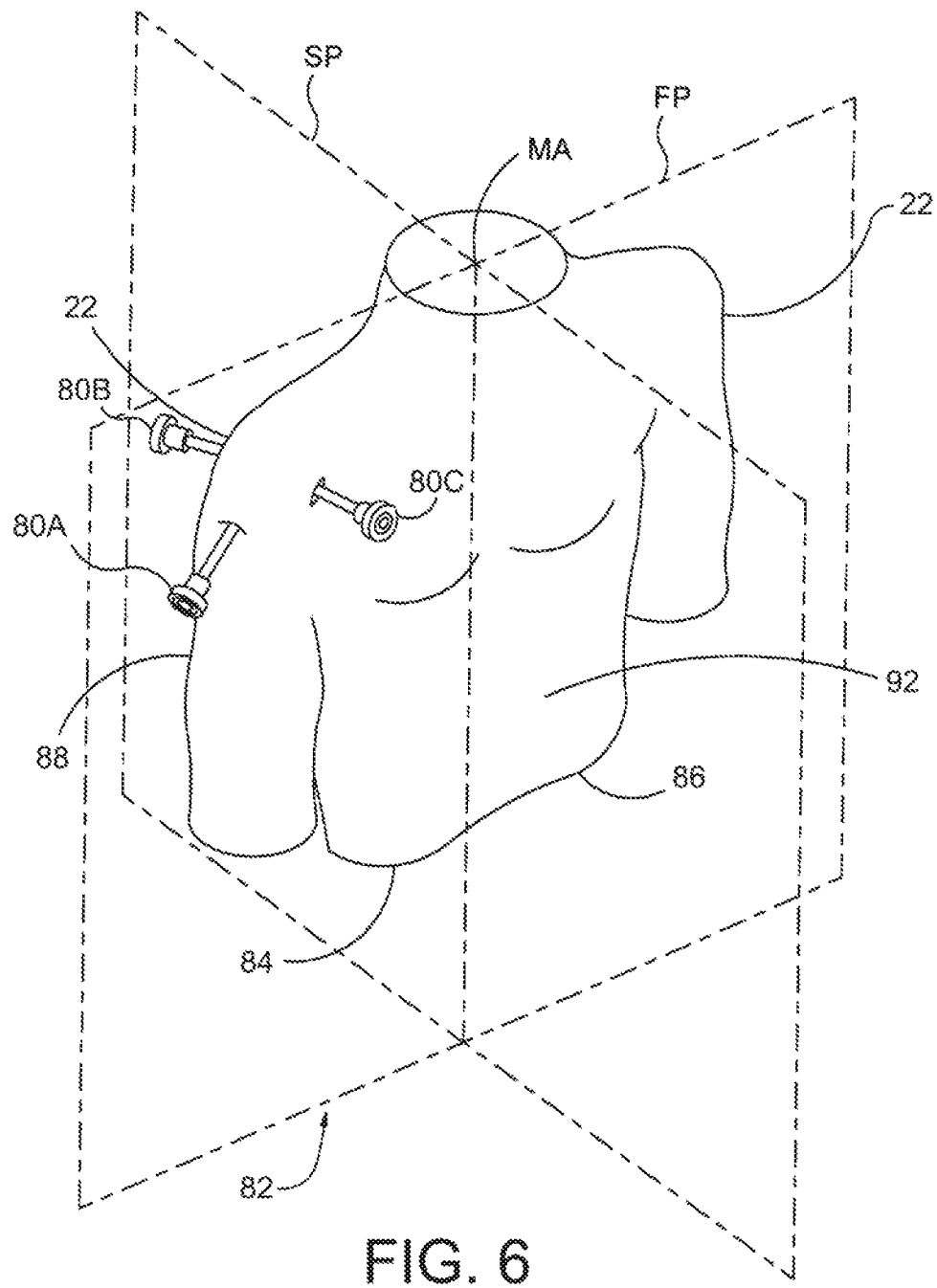
FIG. 6 is a stylized perspective view showing a portion of the body of a human patient divided into quadrants by planes for descriptive purposes herein.

FIG. 6 is a stylized perspective view showing a portion of the body 82 of a human patient 20. Body 82 includes a shoulder 22. In the exemplary embodiment of FIG. 6, a plurality of cannulas are positioned to access a treatment site within shoulder 22. In some cases, shoulder 22 may be inflated by pumping a continuous flow of saline through shoulder 22 to create a cavity proximate the treatment site. The cannulas shown in FIG. 6 include a first cannula 80A, a second cannula 80B and a third cannula 80C.

In FIG. 6, a sagital plane SP and a frontal plane FP are shown intersecting body 82. Sagital plane SP and frontal plane FP intersect one another at a medial axis MA of body 82. With reference to FIG. 6, sagital plane SP bisects body 82 into a right side 84 and a left side 86. Also with reference to FIG. 6, frontal plane FP divides body 82 into an anterior portion 92 and a posterior portion 88. Sagital plane SP and a frontal plane FP are generally perpendicular to one another. These planes and portions are used to describe the procedures used in exemplary embodiments.

First cannula 80A is accessing a treatment site within shoulder 22 using a lateral approach in which first cannula 80A pierces the outer surface of right side 84 of body 82. The term lateral approach could also be used to describe situations in which an instrument pierces the outer surface of left side 86 of body 82. Second cannula 80B is accessing a treatment site within shoulder 22 using a posterior approach in which second cannula 80B pierces the outer surface of posterior portion 88 of body 82. Third cannula 80C is accessing a treatment site within shoulder 22 using an anterior approach in which third cannula 80C pierces the outer surface of anterior portion 92 of body 82.

Figure 7:
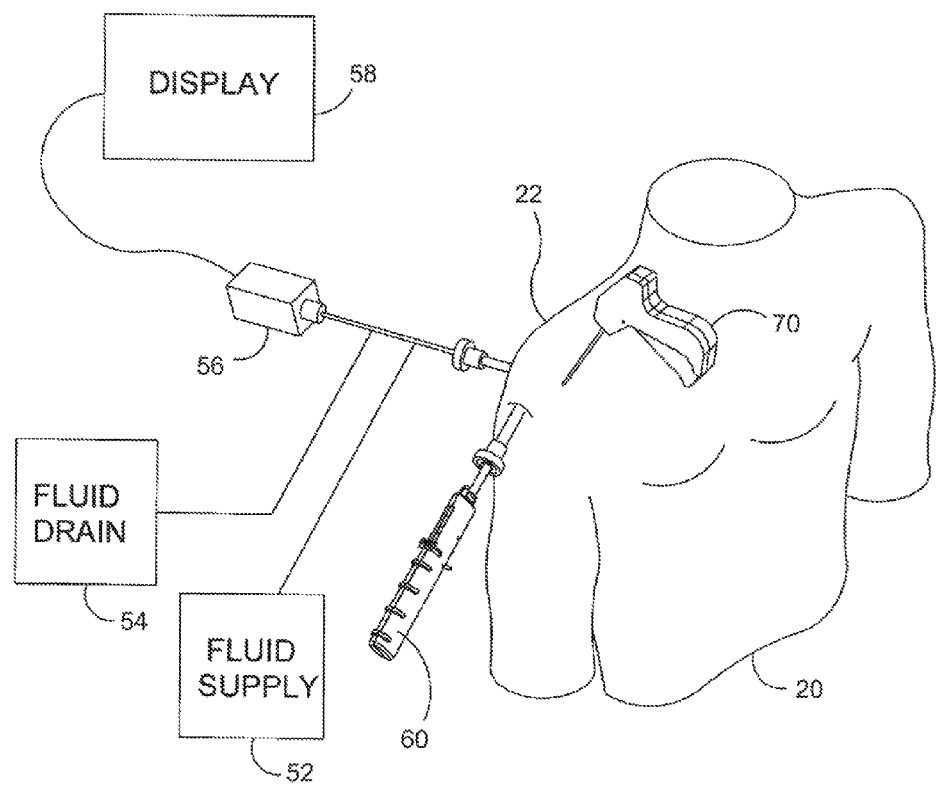
FIG. 7 is a stylized perspective view illustrating an exemplary procedure for arthroscopic treatment of a shoulder of a patient in accordance with one embodiment of the disclosure.

FIG. 7 is a stylized perspective view illustrating an exemplary procedure for treating a shoulder 22 of a patient 20. The procedure illustrated in FIG. 7 may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 7 has been inflated to create a cavity therein. A fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be affixed to a bursal surface of the tendon regardless of whether there are visible signs of tendon damage. Applicants believe that the methods and apparatus of the present application and related devices may provide very beneficial therapeutic effect on a patient experiencing joint pain believed to be caused by internal microtears, but having no clear signs of tendon tears. By applying a tendon repair implant early before a full tear or other injury develops, the implant may cause the tendon to thicken and/or at least partially repair itself, thereby avoiding more extensive joint damage, pain, and the need for more extensive joint repair surgery.

An implant delivery system 60 can be seen extending from shoulder 22 in FIG. 7. Implant delivery system 60 is extending through a first cannula 80A. In certain embodiments, first cannula 80A can access a treatment site within shoulder 22 using a lateral approach in which first cannula 80A pierces the outer surface of a right side of the patient's body. In some cases a physician may choose not to use a cannula in conjunction with implant delivery system 60. When that is the case, the implant delivery system may be advanced through tissue. Implant delivery system 60 comprises a sheath that is affixed to a handle. The sheath defines a lumen and a distal opening fluidly communicating with the lumen. In the embodiment of FIG. 7, the distal opening of the sheath has been placed in fluid communication with the cavity created in shoulder 22.

A tendon repair implant is at least partially disposed in the lumen defined by the sheath of implant delivery system 60. Implant delivery system 60 can be used to place the tendon repair implant inside shoulder 22. In some embodiments, the tendon repair implant is folded into a compact configuration when inside the lumen of the sheath. When this is the case, implant delivery system 60 may be used to unfold the tendon repair implant into an expanded shape. Additionally, implant delivery system 60 can be used to hold the tendon repair implant against the tendon.

The tendon repair implant may be affixed to the tendon while it is held against the tendon by implant delivery system 60. Various attachment elements may be used to fix the tendon-repair implant to the tendon. Examples of attachment elements that may be suitable in some applications include sutures, tissue anchors, bone anchors, and staples. In the exemplary embodiment of FIG. 7, the shaft of a fixation tool 70 is shown extending into shoulder 22. In one exemplary embodiment, fixation tool 70 is capable of fixing the tendon repair implant to the tendon and bone with one or more staples of the present disclosure while the tendon repair implant may held against the tendon by implant delivery system 60.

Figure 8:
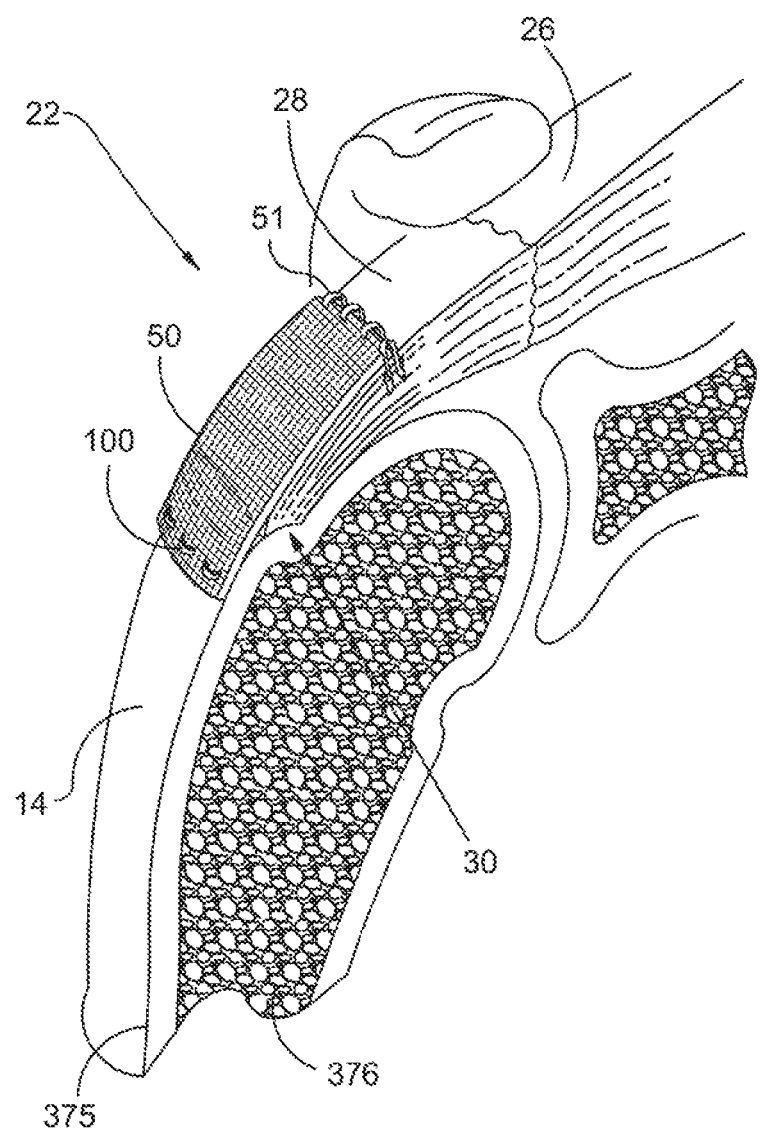
FIG. 8 is a stylized perspective view of a shoulder including a supraspinatus having a distal tendon with a sheet-like material affixed thereto.

FIG. 8 is a stylized perspective view of a shoulder 22 including a supraspinatus 26 having a distal tendon 28. With reference to FIG. 8, a tendon repair implant 50 has been affixed to a surface of distal tendon 28. Tendon repair implant 50 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some embodiments, the sheet-like structure may comprise a laminate including multiple layers of film with each layer of film defining a plurality of micro-machined or formed holes. The sheet-like structure of the tendon repair implant may also comprise a reconstituted collagen material having a porous structure. Additionally, the sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Fremont, Calif. which identifies these materials using the trademark BIOMATERIAL™. The sheet-like structure may be circular, oval, oblong, square, rectangular, or other shape configured to suit the target anatomy.

Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the embodiment of FIG. 9, sheet-like implant 50 is affixed to distal tendon 28 by a plurality of tendon staples 51. Sheet-like implant 50 is affixed to humerus 14 by a plurality of bone staples 100 as described with respect to the exemplary embodiment of FIG. 1 and detailed throughout this disclosure.

In some exemplary methods, a plurality of staples may be applied using a fixation tool. After the staples are applied, the fixation tool may be withdrawn from the body of the patient. Distal tendon 28 meets humerus 14 at an insertion point 30. With reference to FIG. 8, it will be appreciated that sheet-like implant 50 extends over insertion point 30. Tendon repair implant may be applied to distal tendon 28, for example, using the procedure illustrated in the previous figures. In various embodiments, staples may straddle the perimeter edge of the sheet-like implant (as shown in FIG. 8), may be applied adjacent to the perimeter, and/or be applied to a central region of the implant. In some embodiments, the staples may be used to attach the implant to soft tissue and/or to bone.

Staples or fasteners 100, as exemplified in FIG. 1 and described and illustrated herein can be used to attach tissue and implants to bone. In at least some embodiments, the staple is generally flexible and includes areas of relative lateral weakness on the portions of the arms. As described above, these areas of increased flexibility provide improved staple retention as these portions allow flexing and bending in response to increasing pullout forces. With this flexibility, the fasteners cannot be pounded or driven into bone or other tissue as a conventional hard staple would be driven into paper, wood, tissue or bone. Therefore, for application of the staple of the present disclosure to affixing tissue or implants to bone, the staple is generally included in a kit that also includes a staple delivery device 200 and a pilot hole forming trocar assembly 300, as schematically illustrated in FIGS. 9A and 9B, respectively.

In general, the staple delivery device 200 can include a handle assembly 201 and a barrel assembly 205. The handle assembly 201 includes a trigger 203 that is operatively coupled to mechanisms in the barrel assembly 205 to deploy a staple of the present disclosure in bone. The staple delivery device 200 can be used in conjunction with the pilot hole forming trocar assembly 300 of FIG. 9B.

Figure 9B:
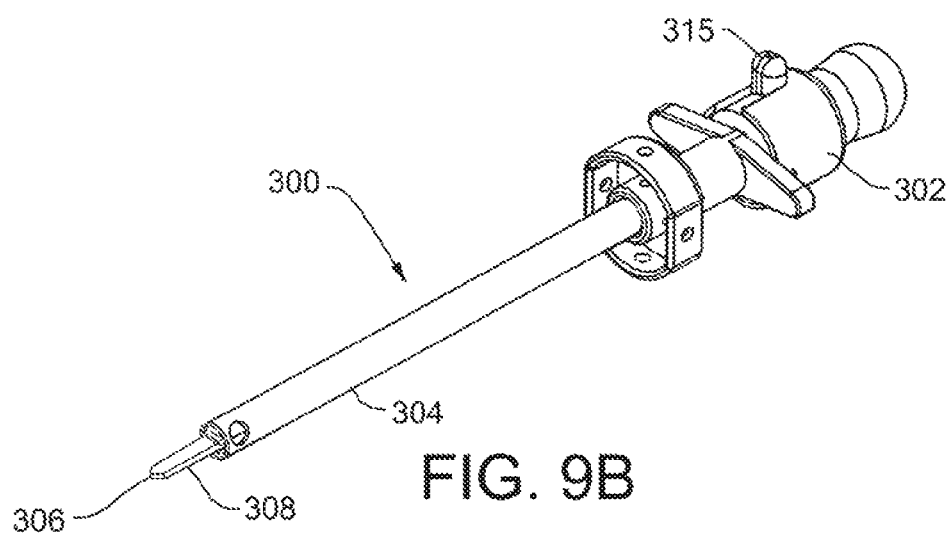
FIG. 9B is a simplified perspective view of a trocar assembly, including a trocar disposed within a guide sheath assembly for creating pilot holes and retaining the sheath within the formed pilot holes for delivery of a tissue fastener or staple by a device such as that depicted in FIG. 9A.
Figure 9A:
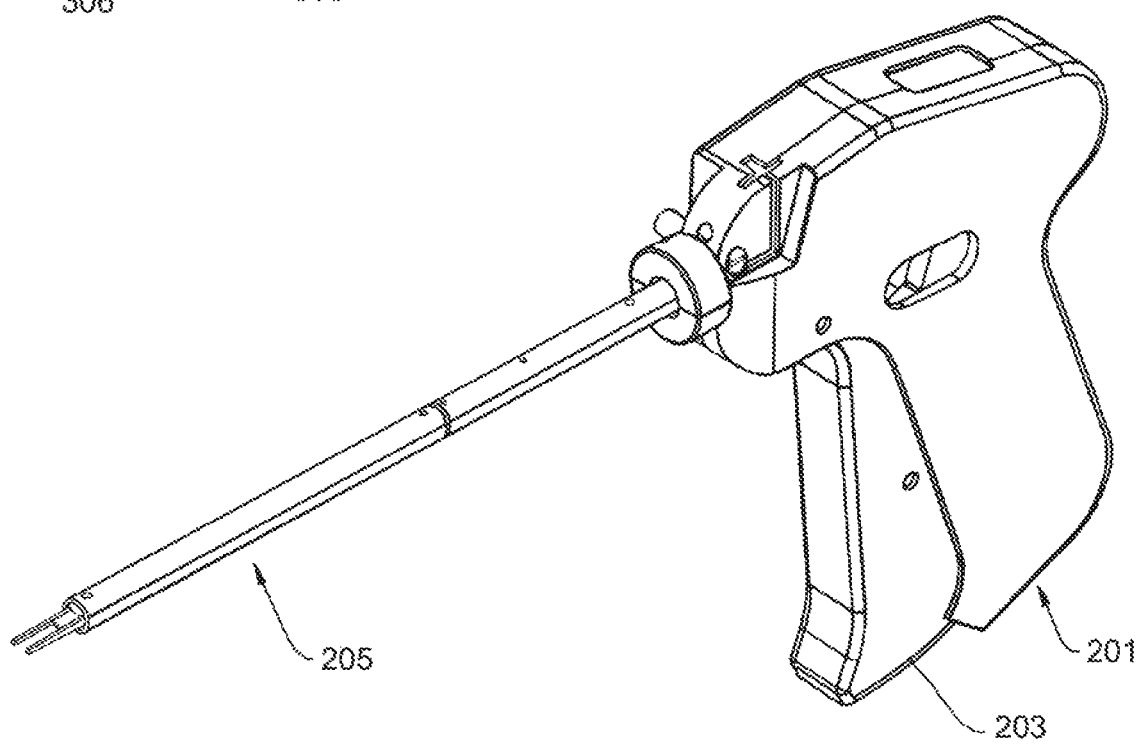
FIG. 9A is a simplified perspective view of a tissue fastener or staple delivery device in accordance with the present disclosure.

The pilot hole forming trocar assembly 300, illustrated generally in FIG. 9B includes a trocar 302 and a position retention sleeve 304. The trocar 302 is releasably coupled to the position retention sleeve 304 and slides in keyed arrangement within the sleeve 304 when uncoupled. The trocar 302 includes a distal portion having a retractable blade 306 and a pair of pilot hole forming spikes 308 extending distally from the trocar shaft. The retractable blade 306 is useful in inserting the assembly through an incision. The retractable blade 306 can be retracted in this exemplary embodiment by activating release button 315 which causes a spring (not shown) to pull the retractable blade 306 into the shaft of the trocar within the position retention sleeve 304. In this position, the pilot hole forming spikes remain extended from the shaft. In some embodiments the retractable blade 306 can be omitted if the pilot hole forming trocar assembly is to be inserted into an incision that already has a cannula extending therethrough to provide an instrument path.

Figure 10A:
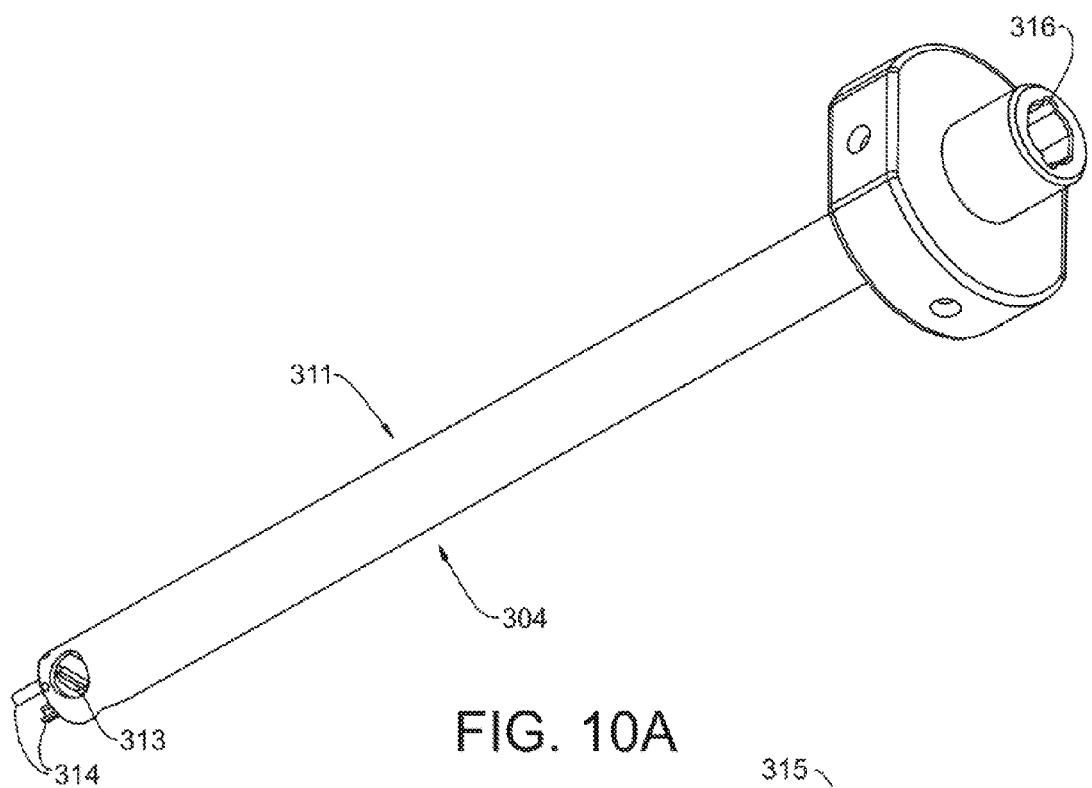
FIG. 10A is a perspective view of the sheath assembly of FIG. 9B with the trocar removed.
Figure 10B:
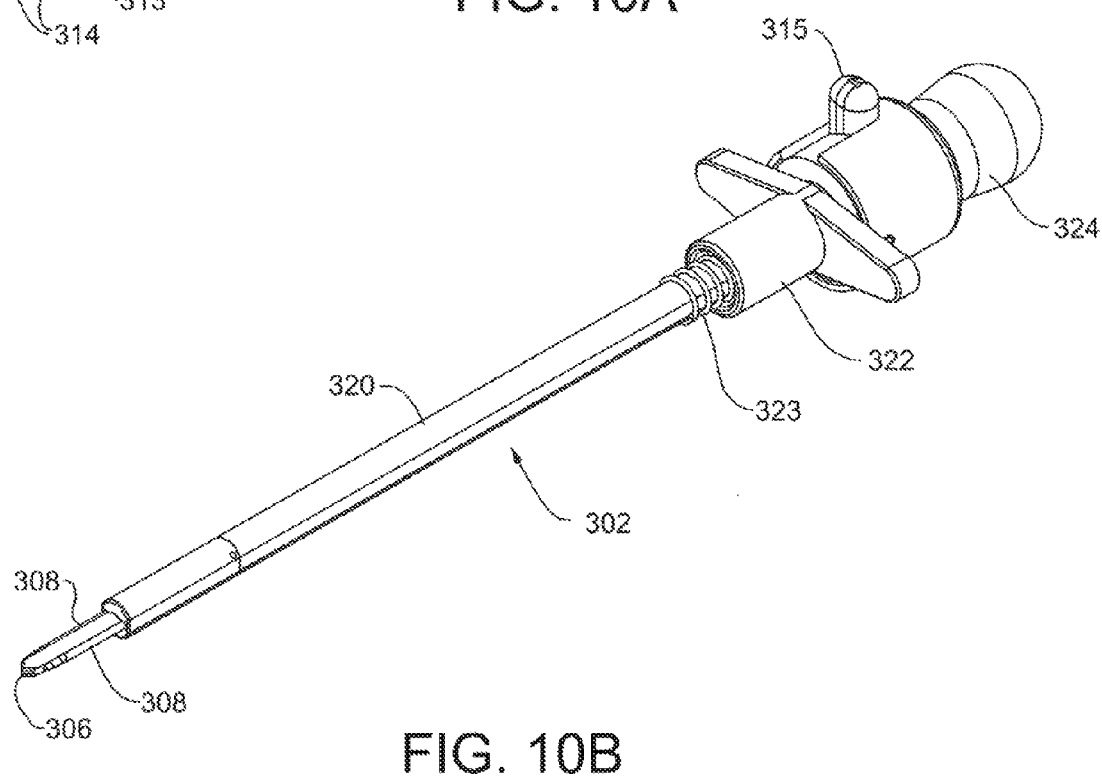
FIG. 10B is a perspective view of the trocar of FIG. 9B as removed from the sheath assembly.
Figure 10C:
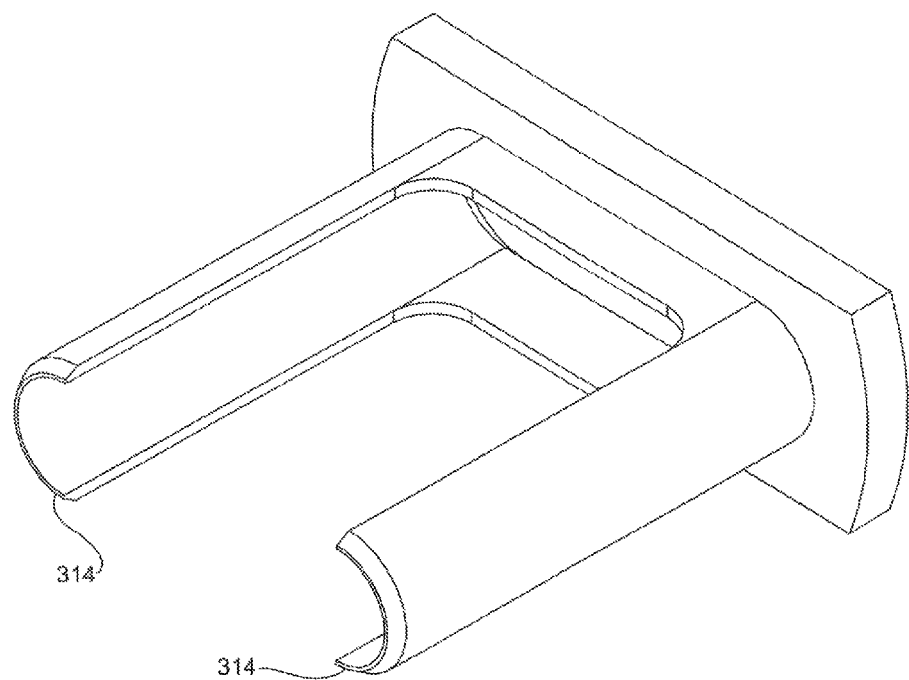
FIG. 10C is a perspective view of one pilot hole position retention member which is positioned in a distal portion of the sheath assembly in one embodiment of the present disclosure.

Referring to FIGS. 10A-10C, details of the elements of one exemplary embodiment of a pilot hole forming trocar assembly 300 are illustrated. The pilot hole forming trocar assembly is used to created pilot holes in a bone for subsequent placement of a staple or fastener, such as staple 100 of FIG. 1. Further, the pilot hole forming trocar assembly includes a means for retaining instrument position with respect to the pilot holes when the trocar is removed so that a staple delivery device 200 can be inserted and the staple be in alignment with the already formed pilot holes. This prevents the time and difficulty associated with finding the pilot holes with the staple, which in fact may not be possible for many practitioners.

As previously stated, a pilot hole forming trocar assembly 300 can include a trocar 302 and a position retention sleeve 304. One embodiment of a position retention sleeve 304 is illustrated in FIG. 10A. The position retention sleeve 304 includes a shaft 311 having a lumen 310 extending therethrough. The lumen 310 is sized to receive the trocar 302 when used to form pilot holes. The lumen 310 is also sized to receive a staple delivery device 200 when used to position a staple in pilot hole formed in bone. The lumen is shaped or keyed to cooperate with either of these instruments or other instruments so that relative rotational position of the trocar 302 or staple delivery device 200 is fixed when slidably positioned in the position retention sleeve. An opening or window 313 may be included near the distal end of the position retention sleeve to allow viewing of devices inserted therein.

Position retention members 314 extend distally from the shaft 311. As detailed in FIG. 10C, the position retention members can be included on an insert 312 that is affixed proximate the distal end of the shaft 311. Alternatively, the position retention members can be integral to the shaft 311. The position retention members are sized and designed to extend into pilot holes as they are formed by the trocar 302 described below. When the trocar 302 is removed, the position retention members 314, along with the sleeve 311 remain in position to provide a guide for the staple delivery device 200 to be inserted into proper position and position a staple 100 in the pilot holes. As depicted, the position retention members 314 can include longitudinally extending semi-cylindrical projections. In the disclosed embodiment, the pilot hole forming spikes 308 of the trocar 302 slide within the partial lumens of the position retention members 314. This design can provide support for the spikes as they are pounded into bone and can also allow the position retention members to readily slide into pilot holes formed by the spikes 308.

A more detailed depiction of one alternative embodiment of a trocar 302 is included in FIG. 10B. The trocar includes a shaft 320 having at its proximal end a knob 324 that can be used to pound or push the trocar 302 into bone. The trocar can further include a collar 322 which can be used to releasable engage the position retention sleeve 304 when the two are mated for forming pilot holes. A spring 323 can be included which causes or aids the retraction of the trocar when it is released from the position retention sleeve.

As previously disclosed, the distal end of the trocar 302 includes two pilot hole forming spikes 308 extending from shaft 320. A retractable blade 306 is positioned between the spikes 308. In use, the blade 306 is retracted prior to the spikes 308 being used to form pilot holes in bone.

Now referring to FIG. 11, a distal portion of a staple delivery device 200, in particular a distal portion of the barrel 205 of FIG. 9A is depicted with a staple 100 mounted thereon for delivery into bone. The parts of the staple are labeled as they are in FIG. 1 with all of the same components numbered the same. In FIG. 11, the barrel 205 has an outer sheath 206 with a staple delivery assembly 207 disposed within the lumen of the sheath 206. The staple delivery assembly 207 can be moved from a retracted position within the sheath 206 to an extended position distal of the sheath 206, as illustrated.

FIG. 12 is a cross sectional view of the distal portion of the staple delivery device 200 depicted in FIG. 11. The staple delivery assembly 207 is illustrated within the lumen of the sheath 206. As seen in both figures, the staple setting rods 210A, 210B have a portion extending beyond the sheath onto which the staple is mounted and carried for delivery. Further, the staple delivery assembly 207 includes a spring 208 engaging a staple pusher 219 having a distal surface 220 engaging the bridge 104. This portion of the staple delivery assembly 207 urges the staple 100 into pilot holes.

The staple setting rods 210 have a proximal portion 212 that includes distal surfaces in abutment with the proximal surfaces of the loops 122. The staple setting rods are actively coupled to the trigger 203 and can be urged distally when the staple is in position. As previously discussed, this action adjusts the staple configuration so that the bridge is in tension and the staple retention members are engaged in competent bone to provide adequate holding strength.

Figure 13A:
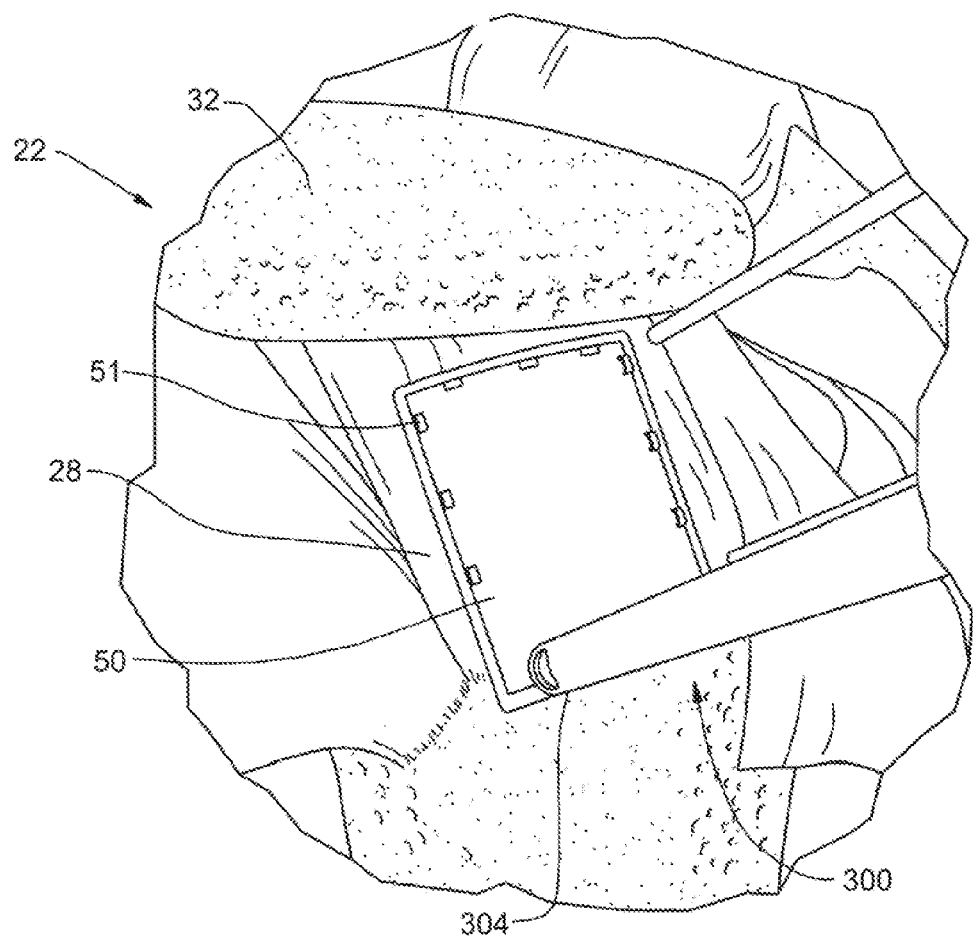
FIG. 13A is simplified perspective view of a shoulder having an implant affixed to the tendon and depicting the first step in a method of delivering fasteners to affix the implant to bone of the humeral head in accordance with one method of the disclosure.

The method of forming pilot holes and delivering staples of the present disclosure to bone is described with respect to FIGS. 13A-13F which depict the various steps in affixing an implant 50 to bone with staples or fasteners of the present disclosure. FIG. 13A schematically depicts a shoulder 22 of a patient 20 having an implant 50 positioned over a supraspinitus tendon 28. The implant is partially affixed to the tendon 28 with fasteners 51 and extends laterally to and over the insertion point of the tendon to the humeral head 24. As depicted, the implant 50 is not yet affixed to the humeral head 24. A distal portion of a pilot hole forming trocar assembly 300, in particular the position retention sleeve 304, is disposed over a desired location near the lateral edge of the implant 50 where it overlies the humeral head 24. It is noted the FIG. 13A is a depiction with all overlying tissue removed from the shoulder 22 to clearly show the location of the entire implant 50 on the supraspinitus tendon 28. This view is not possible during actual arthroscopic procedures in which the fasteners and instruments of the present disclosure can be used, however the depiction provides a clear understanding of the placement of an implant and the use of fasteners disclosed herein. In actual use the surgeon will have a side view from a viewing scope (not shown) of a small space created by inflating the area with fluid and clearing necessary obstructions from the implant area.

Figure 13B:
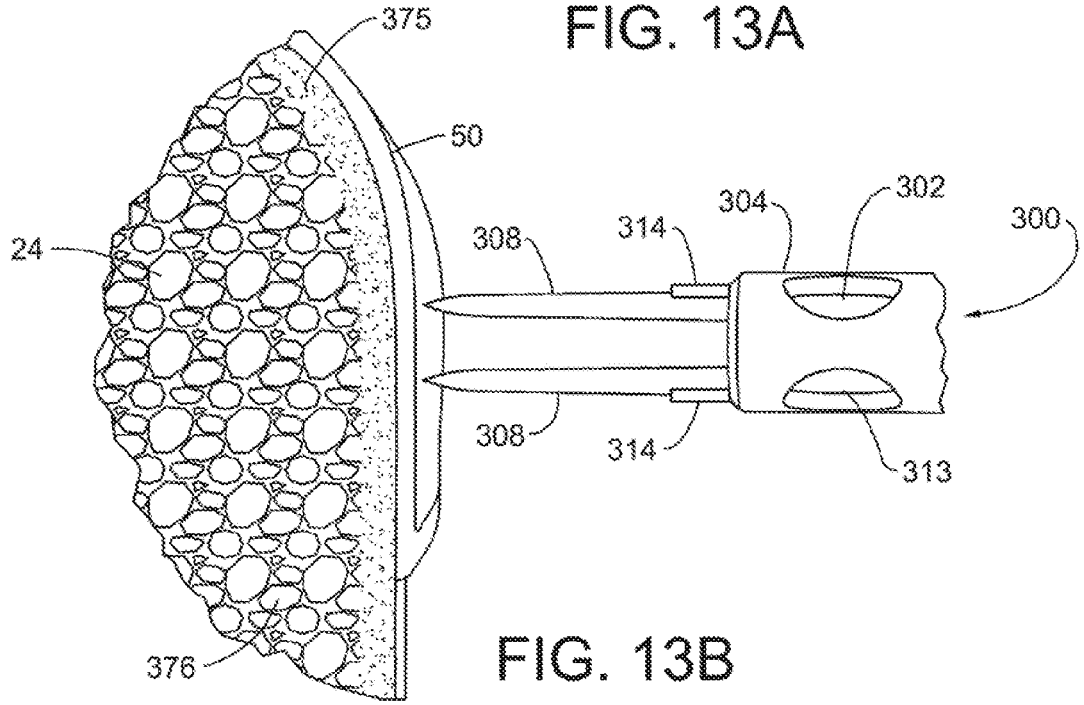
FIG. 13B is a simplified plan view of the distal portion of the trocar assembly as position to create pilot holes for affixing the implant to bone in a further step of a method of the disclosure.

FIG. 13B is a schematic illustration of a cross-sectional side view of the partially affixed implant of FIG. 13A showing the small portion of the implant 50 that is not yet affixed to the humeral head 24. As can be seen in the illustration, the humeral head 24 is shown in cross-section which illustrates the composite nature of bone structure. In general, bone includes hard outer portion or cortical layer 375 and a porous softer inner portion or cancellous bone 376. The pilot hole forming trocar assembly 300 is positioned with the spikes 308 over a selected position on the implant 50. As previously discussed, the trocar 302 is positioned within the lumen of the position retention sleeve 304 with spikes 308 extending distally. The spikes 308 can be used to manipulate and position the implant as needed. Once in position, the spikes 308 can be driven into the bone.

Figure 13C:
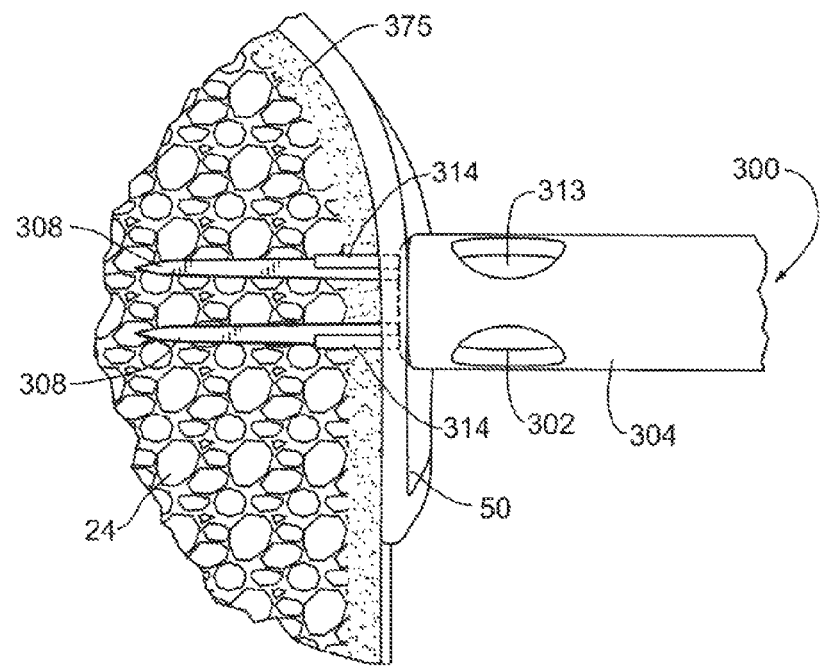
FIG. 13C depicts the trocar assembly of FIG. 13B as inserted into the bone to form pilot holes in accordance with a method of the disclosure.
Figure 13D:
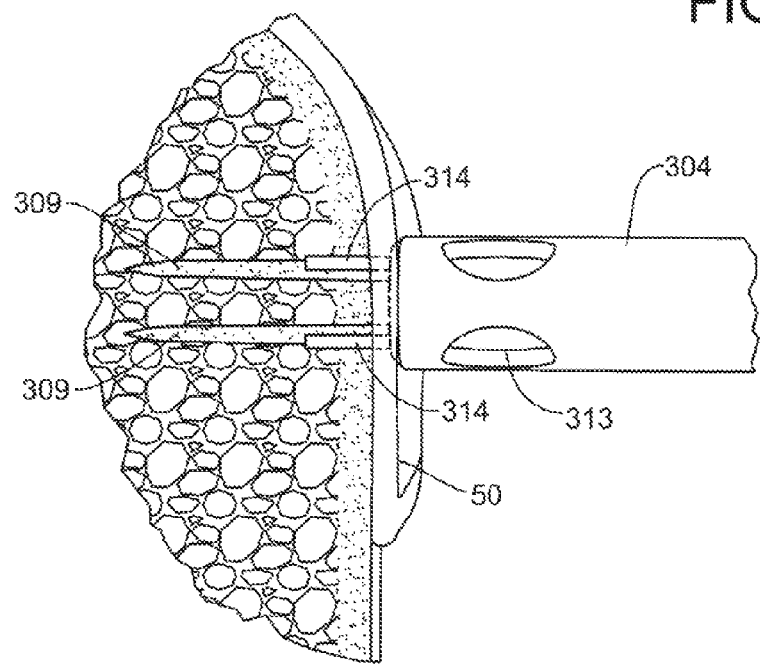
FIG. 13D depicts the trocar assembly with the trocar portion removed and the remaining sheath assembly retaining its position in the pilot holes formed.
Figure 13E:
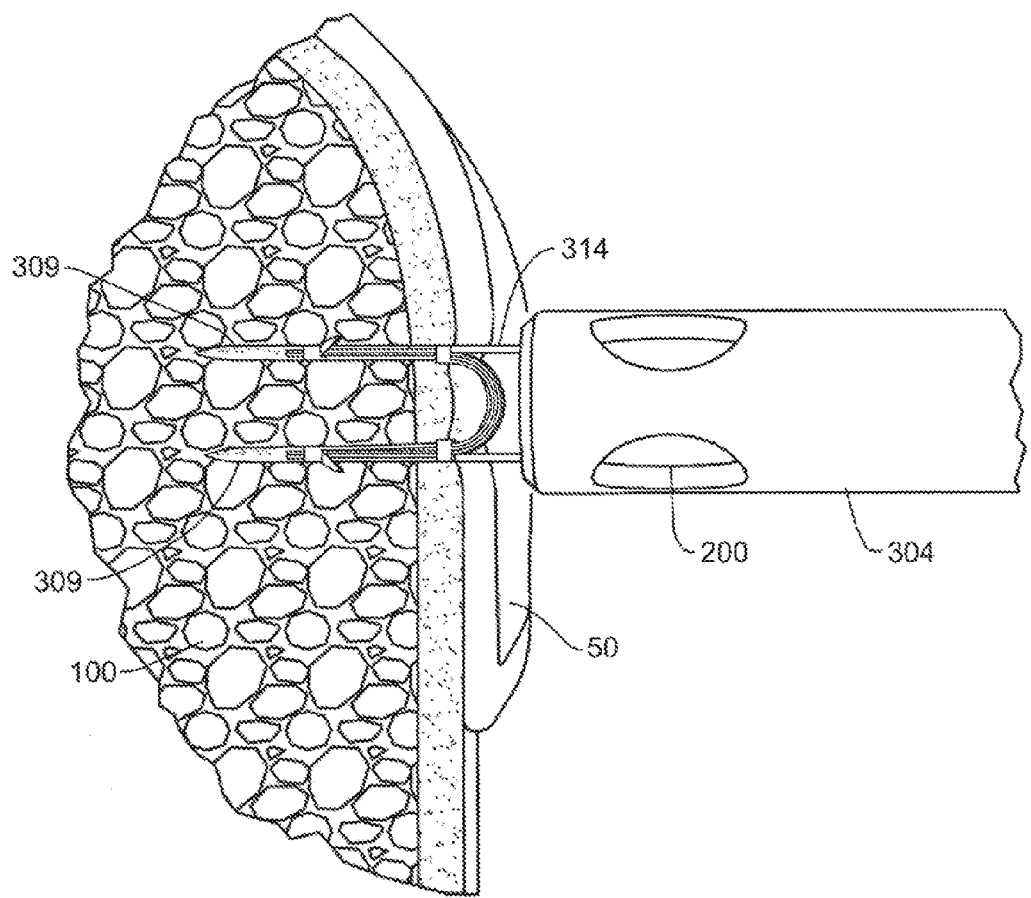
FIG. 13E depicts insertion of a fastener or staple into the formed pilots holes through the sheath assembly in accordance with a method of the disclosure; and, FIG. 13F illustrates a fastener or staple as inserted in accordance with a method of the disclosure.
Figure 13F:
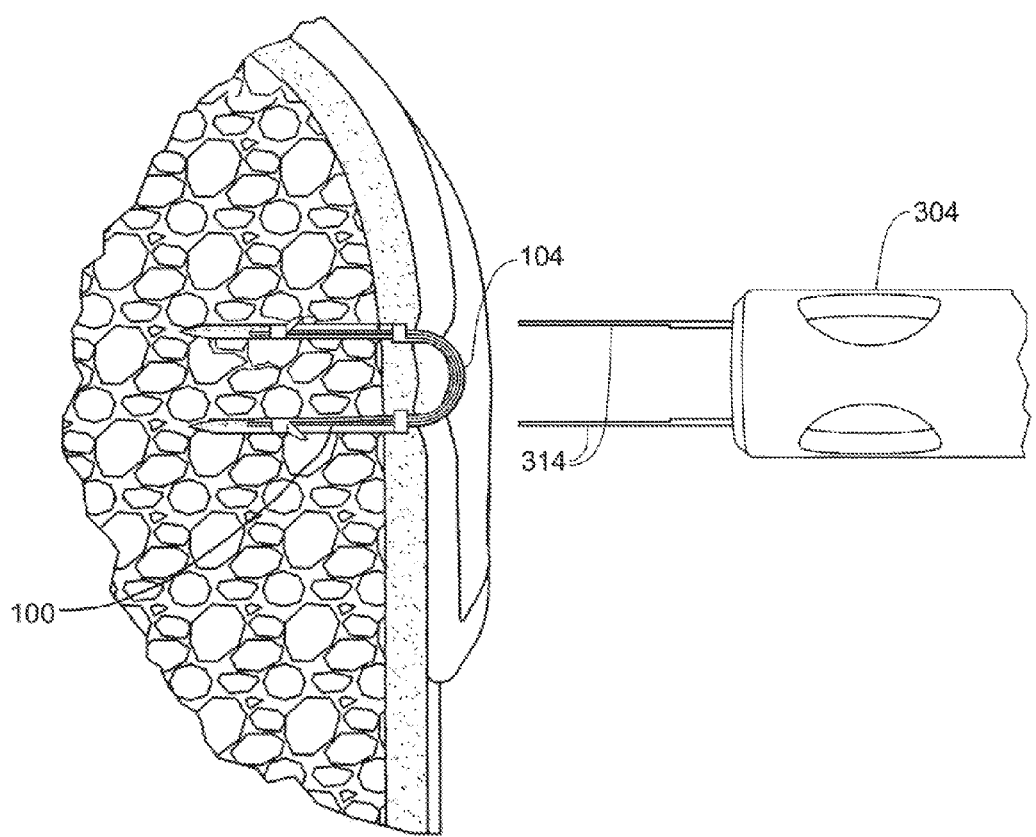

Referring to FIG. 13C, the illustration of FIG. 13B is re-illustrated with the pilot hole forming trocar 300 spikes pounded or otherwise driven into the humeral head 24, penetrating the cortical layer 375 into the cancellous portion 376. As illustrated, position retention members 314 also penetrate the bone with the spikes 308. In FIG. 13D, it is illustrated that the trocar 302 and its distal spikes 308 are now removed leaving formed pilot holes 309 with the position retention sleeve 304 remaining in position with position retention member 314 extending into pilot holes 309. The position retention member 304 lumen provides a guide to the pilot holes 309 for a staple delivery device 200. In FIG. 13E, a staple 100 is shown extending into the pilot holes 309 as mounted on the distal end of a staple delivery device 200 that has been inserted into the lumen of position retention member 304. In this position the staple can be delivered and retained in the bone as previously described in the various embodiments disclosed herein. In delivering the staple 100, the staple delivery assembly distal surface pushes on the bridge of the staple while the proximal portion of the staple setting rods is urged distally relative to the surface. This action of the staple delivery assembly on the proximal surface of the loop of each leg will caused the staple to adjust to a tensioned configuration. Two adjustments may occur. First, the proximal portion of the arms may draw down on the implant. Second, if either of the staple retention members are not secure in bone, they will move proximally within the pilot hole until bone is grasped and counters the force on the proximal surface of the loop. This may include the staple retention member moving proximally to the interface between cancellous and cortical bone, particularly if the staple is placed in a more porous bone structure, such as in an elderly person. FIG. 13F depicts a staple 100 as delivered into bone with bridge 304 holding the implant in position on the bone and arms of the staple retaining position in the in the bone, such as within the cancellous portion 376.

While exemplary embodiments of the present invention have been shown and described, modifications may be made, and it is therefore intended in the appended claims and subsequently filed claims to cover all such changes and modifications which fall within the true spirit and scope of the invention.

What is claimed is:

1. A fastener delivery tool comprising:
   a barrel assembly having an outer sheath with a staple delivery assembly disposed therein, the staple delivery assembly including a shaft having a distal surface for the engagement of a bridge portion of a staple when mounted on the delivery tool;
   the staple delivery assembly further including first and second staple setting rods each having stake portions extending distally beyond the distal surface, wherein each stake portion includes a distal portion sized for sliding engagement of a tissue retention member and a proximal portion having a surface abutting a loop member on a staple arm for applying distally directed force to the loop to achieve a desired configuration of the staple retained in tissue when the stake portions are moved distally relative to the distal surface; and
   a handle assembly fixed to the outer sheath of the barrel assembly in an operative relationship with the staple delivery assembly.

2. The fastener delivery tool of claim 1, wherein the staple delivery assembly is longitudinally extendable from a first position enclosed within the outer sheath to a second position wherein at least a portion of the staple delivery assembly extends distally from the outer sheath.

3. The fastener delivery tool of claim 1, wherein the staple delivery assembly includes a proximal shaft portion having a proximal portion of the first and second staple setting rods fixed thereto and a distal portion with a spring therebetween to allow relative longitudinal movement between the distal surface and the first and second staple setting rods in response to increased force applied to the proximal shaft portion.

4. The fastener delivery tool of claim 3, wherein at least a portion of each of the first and second staple setting rods has a cross sectional shape that slidingly engages a channel of like cross-sectional shape on the staple delivery assembly to restrict relative motion of the distal surface and staple setting rods in a longitudinal direction.

5. A delivery tool for surgical staples comprising:
an outer sheath including a position retention sleeve positioned at a distal end thereof and a lumen extending therethrough;
a longitudinally extendable staple delivery assembly disposed within the lumen of the outer sheath; and
a handle assembly coupled to a proximal portion of the outer sheath, wherein the handle assembly includes a trigger operatively coupled to the staple delivery assembly;
wherein the lumen of the outer sheath is sized and adapted to successively receive a pilot hole trocar and the longitudinally extendable staple delivery assembly;
the longitudinally extendable staple delivery assembly further comprising:
first and second staple setting rods each having a distal end extendable distally beyond the outer sheath and a proximal portion including a shoulder sized and adapted to abut a proximal surface of a surgical staple,
wherein the first and second staple setting rods are actively coupled to the trigger for advancement relative to the position retention sleeve; and
wherein operation of the trigger of the handle assembly advances the first and second staple setting rods distally to deliver the surgical staple.

6. The delivery tool of claim 5, wherein the staple delivery assembly further comprises:
a staple pusher having a distal surface sized and adapted to engage a bridge of the surgical staple.

7. The delivery tool of claim 6, wherein the staple delivery assembly further comprises a spring which advances the staple pusher when the first and second staple setting rods are advanced distally.

8. The delivery tool of claim 5, wherein the proximal surface of the surgical staple is a loop of the surgical staple.

9. The delivery tool of claim 5, wherein the position retention sleeve includes first and second semi-cylindrical portions sized and adapted to receive and guide the first and second staple setting rods, respectively, when the first and second staple setting rods are advanced distally.

10. The delivery tool of claim 9, wherein the first and second semi-cylindrical portions of the position retention sleeve are sized and adapted to enter first and second pilot holes, respectively, in tissue to be stapled.

11. The delivery tool of claim 10, further comprising a trocar advanceable through the lumen of the outer sheath and distally from the outer sheath to form the first and second pilot holes.

12. The delivery tool of claim 11, wherein the position retention sleeve is shaped or keyed to cooperate with the trocar such that a rotational orientation of the trocar is fixed when slidably positioned in the lumen of the outer sheath.

13. The delivery tool of claim 5, wherein the position retention sleeve is shaped or keyed to cooperate with the staple delivery assembly such that a rotational orientation of the staple delivery assembly is fixed when slidably positioned in the lumen of the outer sheath.

* * * * *